United States Patent [19]

Wohlleben et al.

[11] Patent Number: 4,992,371
[45] Date of Patent: Feb. 12, 1991

[54] HYBRID PLASMIDS HAVING A STREPTOMYCETES REPLICON AND AN ESCHERICHIA COLI REPLICON

[75] Inventors: Wolfgang Wohlleben; Günter Muth; Alfred Pühler, all of Bielefeld, Fed. Rep. of Germany

[73] Assignee: Hoechst Aktiengesellschaft, Frankfurt, Fed. Rep. of Germany

[21] Appl. No.: 372,229

[22] Filed: Jun. 26, 1989

Related U.S. Application Data

[63] Continuation of Ser. No. 111,105, Oct. 14, 1987, abandoned, which is a continuation of Ser. No. 717,846, Mar. 29, 1985, abandoned.

[30] Foreign Application Priority Data

Mar. 31, 1984 [DE] Fed. Rep. of Germany ....... 3412093

[51] Int. Cl.$^5$ .................... C12N 15/00; C12N 1/20
[52] U.S. Cl. ..................... 435/172.3; 435/252.33; 435/252.35; 435/320.1; 935/21; 935/73; 935/75
[58] Field of Search ................. 435/91, 171.1, 172.3, 435/320, 849, 886, 69.1, 71.2, 252.3, 252.33, 252.35; 935/29, 72, 73, 75; 536/27

[56] References Cited

U.S. PATENT DOCUMENTS

| | | | |
|---|---|---|---|
| 4,332,900 | 6/1982 | Manis et al. | 435/172.3 |
| 4,338,400 | 7/1982 | Manis et al. | 435/172.3 |
| 4,340,674 | 7/1982 | Manis et al. | 435/172.3 |
| 4,343,906 | 8/1982 | Reusser et al. | 435/253 |
| 4,360,597 | 11/1982 | Bibb et al. | 435/253 |
| 4,362,816 | 12/1982 | Reusser | 435/172.3 |
| 4,362,817 | 12/1982 | Reusser | 435/172.3 |
| 4,393,137 | 7/1983 | Manis et al. | 435/172.3 |
| 4,401,761 | 8/1983 | Manis et al. | 435/172.3 |
| 4,416,994 | 11/1983 | Nakatsukasa et al. | 435/253 |
| 4,621,061 | 11/1986 | Pühler et al. | 435/172.3 |
| 4,673,642 | 6/1987 | Pühler et al. | 435/68 |

FOREIGN PATENT DOCUMENTS

| | | | |
|---|---|---|---|
| 0035914 | 9/1981 | European Pat. Off. | 435/172.3 |
| 0077649 | 4/1983 | European Pat. Off. | 435/172.3 |
| 0085548 | 8/1983 | European Pat. Off. | 435/172.3 |
| 0092388 | 10/1983 | European Pat. Off. | 435/172.3 |

OTHER PUBLICATIONS

Puehler et al., "Plasmid pSVH1 and Its Use", Chem. Abstr. 98:138431w (1983) of Ger. Offen. DE 3,128,669 (03 Feb. 1983).

Wohlleben et al., "Development of Shuttle Vectors Between Streptomyces Species and Escherichia Coli", Chem. Abstr. 105:1423p (1986) of Eur. Congr. Biotechnol. 3rd (1984) 3:219–224.

Wohlleben et al., "Streptomyces Plasmid pSG5 and Its Use", Chem. Abstr. 104:46699d (1986) of Eur. Pat. Appl. EP 158,872.

Schottel et al., Cloning and Expression in Streptomyces Lividans of Antibiotic Resistance Genes Derived from Escherichia Coli, J. Bact. vol. 146, No. 1, pp. 360–368 (Apr. 1981).

Kieser et al., PIJ101, a Multi-copy Broad Host-Range Streptomyces Plasmid, Mol. Gen. Gent. vol. 185, pp. 223–238 (1982).

Chater et al., Gene Cloning in Streptomyces, Current Top. Microbio. Immunol., vol. 96, pp. 69–95 (1982).

*Primary Examiner*—James Martinell
*Attorney, Agent, or Firm*—Finnegan, Henderson, Farabow, Garrett, and Dunner

[57] ABSTRACT

Starting from the Streptomycetes plasmids pSG2, pSG5 and pSVH1, "shuttle vectors" which, in additon to a E. coli replicon, also contain suitable selection markers for E. coli and Streptomycetes are constructed. These shuttle vectors replicate both in E. coli and in Streptomycetes, and they can be used for cloning and expression of foreign DNA.

6 Claims, 20 Drawing Sheets

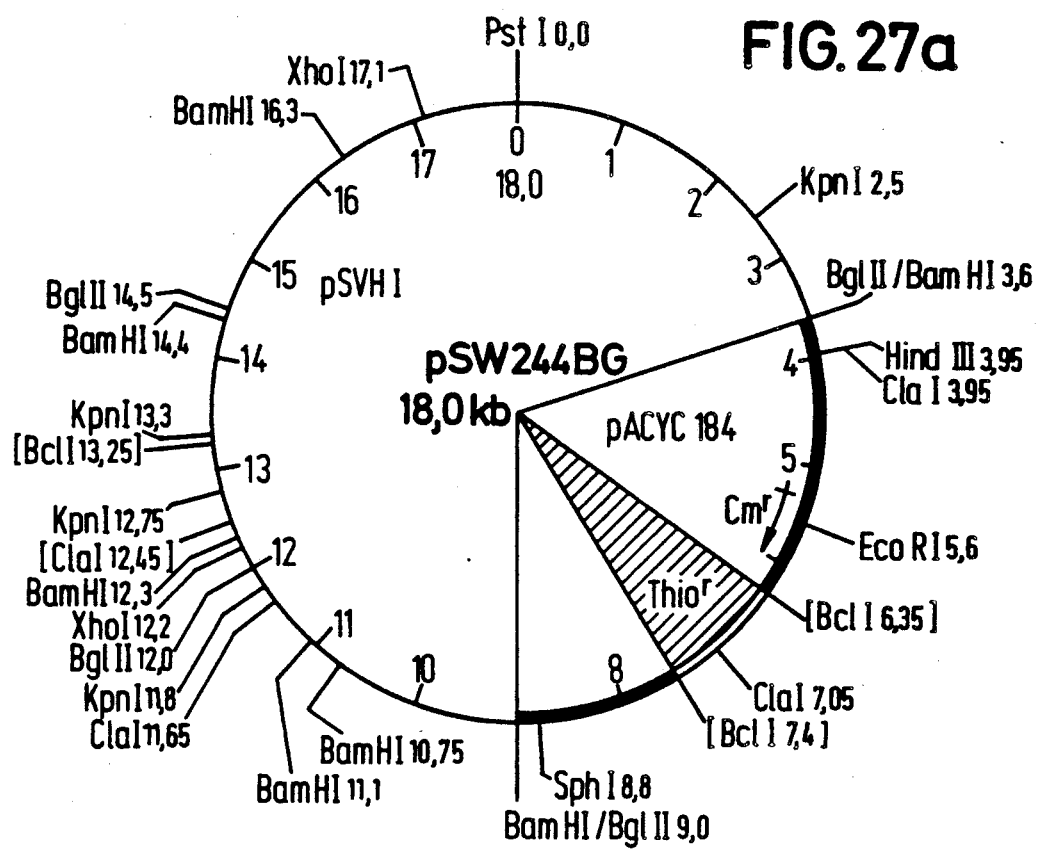

HYBRID PLASMIDS HAVING A STREPTOMYCETES REPLICON AND AN ESCHERICHIA COLI REPLICON

CROSS REFERENCE TO RELATED APPLICATION

This application is a continuation of application Ser. No. 07/111,105, filed Oct. 14, 1987, now abandoned, which is a continuation of application Ser. No. 717,846, filed Mar. 29, 1985, now abandoned.

BACKGROUND OF THE INVENTION

The invention relates to hybrid plasmids, in particular so-called shuttle vectors, which are produced by fusion of *E. Coli* plasmids and the Streptomycetes plasmids pSG2 (European Patent Application with the Publication No. 66,701), pSVH1 (European Patent Application with the Publication No. 70,522) and pSG5 (to which German Patent Application P 34 12 092.0 with the title "The Streptomycetes plasmid pSG5, a process for obtaining it and its use", which was filed on the same date, relates, and which is characterized by FIG. 1), and which therefore undergo autonomous replication both in *E. coli* and in Streptomycetes. Furthermore, the shuttle vectors according to the invention contain markers, preferably resistance genes, which permit selection in Streptomycetes and/or *E. coli*. Hence these shuttle vectors permit the application of tested methods of genetic engineering in *E. coli*, the transfer back into Streptomycetes and the investigation and utilization of manipulated genes in Streptomycetes. Other aspects and preferred embodiments of the invention are illustrated in detail below.

SUMMARY

In accordance with the disclosed invention, a hybrid plasmid is provided which contains an *E. coli* replicon and a Streptomycetes replicon, derived from the plasmid pSG2, pSG5, or pSVH1. The invention also provides a process for preparing such hybrid plasmids.

The starting plasmids used for the *E. coli* contribution are known *E. coli* plasmids, preferably the plasmids pBR322 and pBR325 known from the literature (Bolivar et al., Gene 2 (1977) 95; Bolivar, Gene 4 (1978) 121) and, in particular, the plasmids of the pAC series, pACYC177 and pACYC184 (Chang et al., J. Bacteriol. 134 (1978) 1141). Because of their small size, 4.0 and 4.3 kb respectively, these pAC plasmids are outstandingly suitable for fusion with Streptomycetes plasmids.

It is possible for the *E. coli* DNA sequences present in the shuttle vectors according to the invention to be either unchanged or modified, for example by incorporation of foreign genes or regulation sequences. Thus, a suitable starting plasmid can be obtained by incorporation of other *E. coli* resistance genes, for example by incorporation of a HindIII fragment from the transposon Tn5 (Jorgensen et al., Mol. gen. Genet. 177 (1977) 65), which carries a gene for neomycin/kanamycin resistance, into the HindIII restriction site of pACYC184, this plasmid having been called pACYC184N (Tab. 3). Of course, *E. coli* plasmids which have been modified in another way but in which the original *E. coli* replication system has been retained are also suitable for the shuttle vectors according to the invention. *E. coli* plasmids modified in this way include those into which another *E. coli* replicon has been inserted, for example one of the abovementioned plasmids of the pAC series.

Modified *E. coli* plasmids having resistance genes which are operative in Streptomycetes are advantageous for the construction of the shuttle vectors. These Streptomycetes resistance genes can also be inserted in a *E. coli* plasmid which has already been modified, for example the thiostrepton resistance from the streptomycetes plasmid pIJ6 (Thompson et al., Nature 286 (1980) 525) can be cloned into the plasmid pBR325d (Tab. 1). In this way, a modified *E. coli* plasmid, called pSLE140, is obtained, and can be used for the contruction of the shuttle vectors according to the invention.

The following may be mentioned as further examples of the modification of the *E. coli* plasmids with Streptomycetes resistance genes: the plasmid pSLE11, into which the neomycin resistance gene from the Streptomycetes plasmid pIJ211 (Kieser et al., Mol. gen. Genet. 185 (1982) 223) has been cloned, and the plasmids pSLE40 and 401, which carry the thiostrepton resistance gene from the Streptomycetes plasmid pIJ6.

Vectors which can be used according to the invention and which are obtained by incorporation of resistance genes from Streptomycetes plasmids and can be employed for the construction of shuttle vectors are listed in Table 1 below:

TABLE 1

| Modified E. coli plasmid | E. coli replicon | Cloning site | Streptomycetes fragment with resistance | Resistance of the modified E. coli plasmid | FIG. |
|---|---|---|---|---|---|
| pSLE11 | pBR325 | BamHI | 6.2 kb BclI fragment of pIJ211 (Neo$^r$) | Ap$^r$, Cm$^r$, Tc$^s$ | 2 |
| pSLE40 | pBR325 | BamHI | 1.1 kb BclI fragment of pIJ6 (Thio$^r$) | Ap$^r$, Cm$^r$, Tc$^s$ | 3 |
| pSLE401 | pBR325 | BclI | 1.1 kb BclI fragment of pIJ6 (Thio$^r$) | Ap$^r$, Cm$^r$, Tc$^r$ | 4 |
| pSLE140 | pBR325d* | BamHI | 1.1 kb BclI fragment of pIJ6 (Thio$^r$) | Ap$^r$, Cm$^s$, Tc$^s$ | 5 |

*pBR325d: pBR325 with deletion of small EcoRI/HindIII fragment

Fusion plasmids according to the invention are specified in Table 2 below:

TABLE 2

| E. coli plasmid | Streptomycetes plasmid | Restriction site | Fusion plasmid | Restriction map of the fusion plasmid |
|---|---|---|---|---|
| pBR325 | pSG2 | HindIII | pSGE1 | 6 |
| | | | pSGE2 | 7 |
| pBR325 | pSVH1 | PstI | pSVE1 | 8 |
| | | | pSVE2 | 9 |
| pBR322 | pSVH1 | PstI | pSVE21 | 10 |
| pBR325 | pSVH1 | BamHI | pSVEN1-4 | 11 |
| pACYC177 | pSVH1 | PstI | pSVE31 | 12 |
| pACYC184 | pSG5 | EcoRI | pSGE55 | 13 |

These plasmids are used, on the one hand, for obtaining Streptomycetes DNA from *E. coli* in a simplified manner, since they are stable in *E. coli* and are present in high copy numbers in the *E. coli* plasmid. On the other hand, they are suitable as precursors for the construction of shuttle vectors.

Table 3 specifies shuttle vectors according to the invention, which have been obtained from modified *E. coli* plasmids (Table 1) and which are based on the *E. coli* replicon pBR325:

TABLE 3

| Streptomycetes plasmid | Modified E. coli plasmid | Shuttle vector | Restriction map (FIG.) |
|---|---|---|---|
| pSVH1 (PstI) | pSLE40 (PstI) | pSW254 (19.5 kb) | 14 |
| pSG5 | pSLE11 | pSW311 | 15 |
| (EcoRI) pSG2 | (EcoRI) pSLE40 | (24.3 kb) pSW154P | 16* |

TABLE 3-continued

| Streptomycetes plasmid | Modified E. coli plasmid | Shuttle vector | Restriction map (FIG.) |
|---|---|---|---|
| (partial PstI) | (PstI) | (20.7 kb) | |

*incomplete in respect of the pSLE40 component, see FIG. 3

There are various possibilities for the fusion of the starting plasmids for each shuttle vector. 4 variants are shown in FIG. 16. The variant pSW154P2-2 was preferably used.

The shuttle vectors, according to the invention, with *E. coli* replica of the pBR series are stable in *E. coli* in every case; no deletions in the Streptomycetes contribution to the plasmid have been observed. pSW254, pSW311 and pSW154P express the relevant resistance in Streptomyces (resistance to thiostrepton or neomycin). The plasmids can be transformed in *S. lividans*; this proves that the replication genes are not specific to the original host. Because of the copy number range, as discussed below and the compatibility of the replicon, both mutually and with pIJ101 and SLP1.2 (U.S. Pat. No. 4,360,597), the shuttle vectors are suitable for the extension of existing vector systems so that complex biosynthetic routes can be cloned stepwise into Streptomyces.

Modified plasmids of the pAC series which carry resistance genes for selection in Streptomycetes and which can be used as precursors for the construction of shuttle vectors are listed in Table 4:

TABLE 4

| Plasmid of the pAC series | Restriction site used for cloning | Cloned fragment with Streptomycetes resistance gene | Modified plasmid of the pAC series | Resistance behavior of the modified plasmid in E. coli | Restriction map (FIG.) |
|---|---|---|---|---|---|
| pACYC184N | BamHI | 3.3 kb BamHI fragment from pIJ2 (Neo') | pSLE10 | Km', Cmr | 17 |
| pACYC184 | " | as above | pSLE16 | Cm' | 18 |
| pACYC184 | " | 6.9 kb BamHI fragment from pIJ6 (thio') | pSLE21 | Cm' | 19 |
| pACYC184 | BclI | 1.1 kb BclI fragment from pIJ6 (Thio') | pSLE41 | Cm', Tc' | 20 |

Among others, the shuttle vectors listed in Table 5 can be constructed using the modified plasmids of the pAC series which are specified in Table 4:

TABLE 5

| Modified plasmid of the pAC series | Restriction | Streptomycetes plasmid | Restriction | Shuttle vector | Restriction map of the shuttle vector (FIG.) |
|---|---|---|---|---|---|
| pSLE10 | EcoRI | pSG5 | EcoRI | pSW361 | 21 |
| pSLE16 | HindIII | pSG2 | HindIII | pSW141 | 22 |
| pSLE21 | " | " | " | pSW142 | 23 |
| pSLE41 | BamHI | " | BclI partial | pSW144BC | 24* |
| pSLE41 | " | " | BglII partial | pSW144BG | 25* |
| pSLE41 | " | " | BglII | pSW1 | 26 |
| pSLE41 | " | pSVH1 | BglII partial | pSW244BG | 27* |
| pSLE41 | " | " | BclI | pSW244 | 28 |
| pSLE41 | EcoRI | pSG5 | EcoRI | pSW344E | 29 |
| pSLE41 | BamHI | " | BclI | pSW344B | 30 |

*incomplete in respect of the pSLE41 contribution, see FIG. 20

There are various possibilities of fusing the starting plasmids for each shuttle vector. The variants are shown in the figures.

BRIEF DESCRIPTION OF THE DRAWINGS

This invention will be better understood by reference to the drawings in which:

FIG. 2a is a restriction map of pSLE 11a;
FIG. 15a is a restriction map of pSW 311a;
FIG. 27a is a restriction map of a variant of pSW 244BG.

Figure 25:
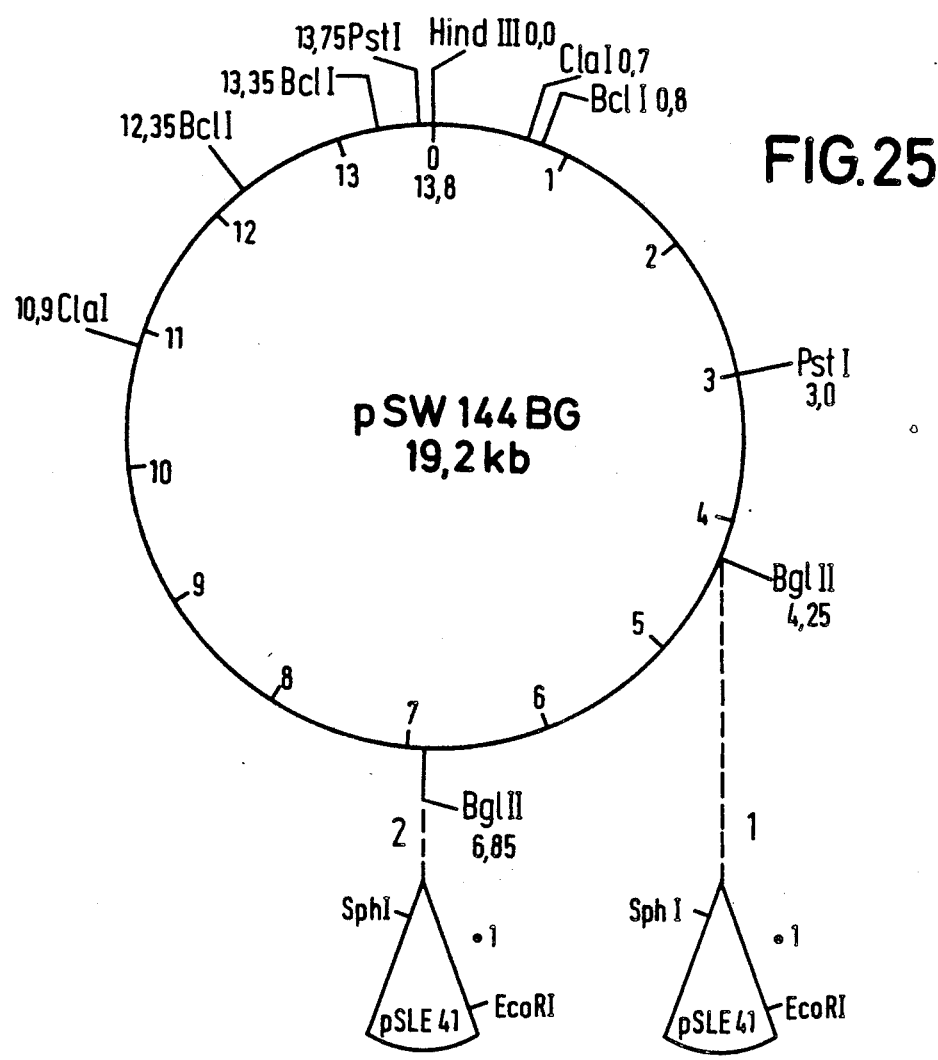
FIG. 25 is a restriction map of pSW 144BG.
Figure 26:
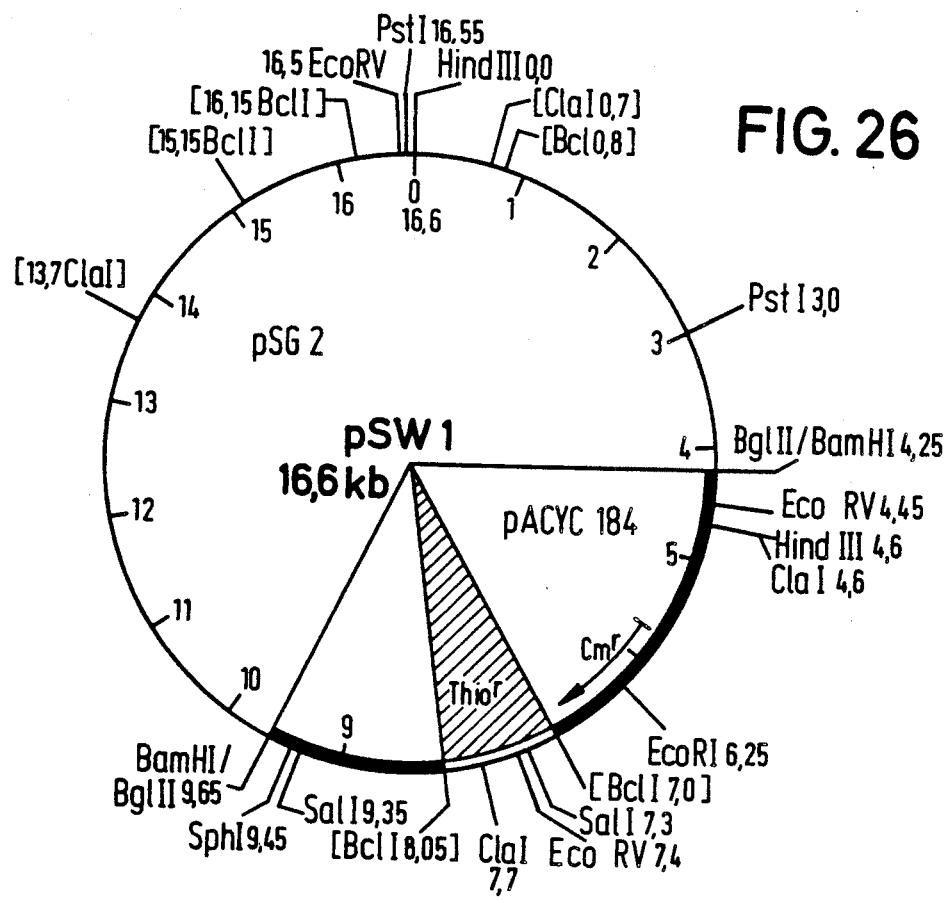
FIG. 26 is a restriction map of pSW 1.
Figure 28:
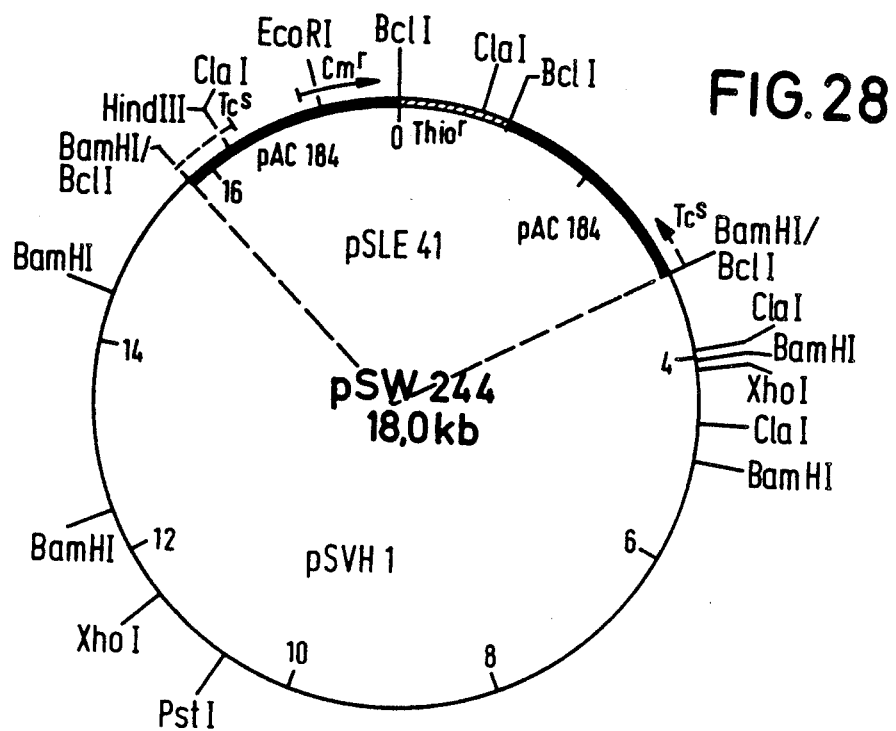
FIG. 28 is a restriction map of pSW 244.
Figure 27:
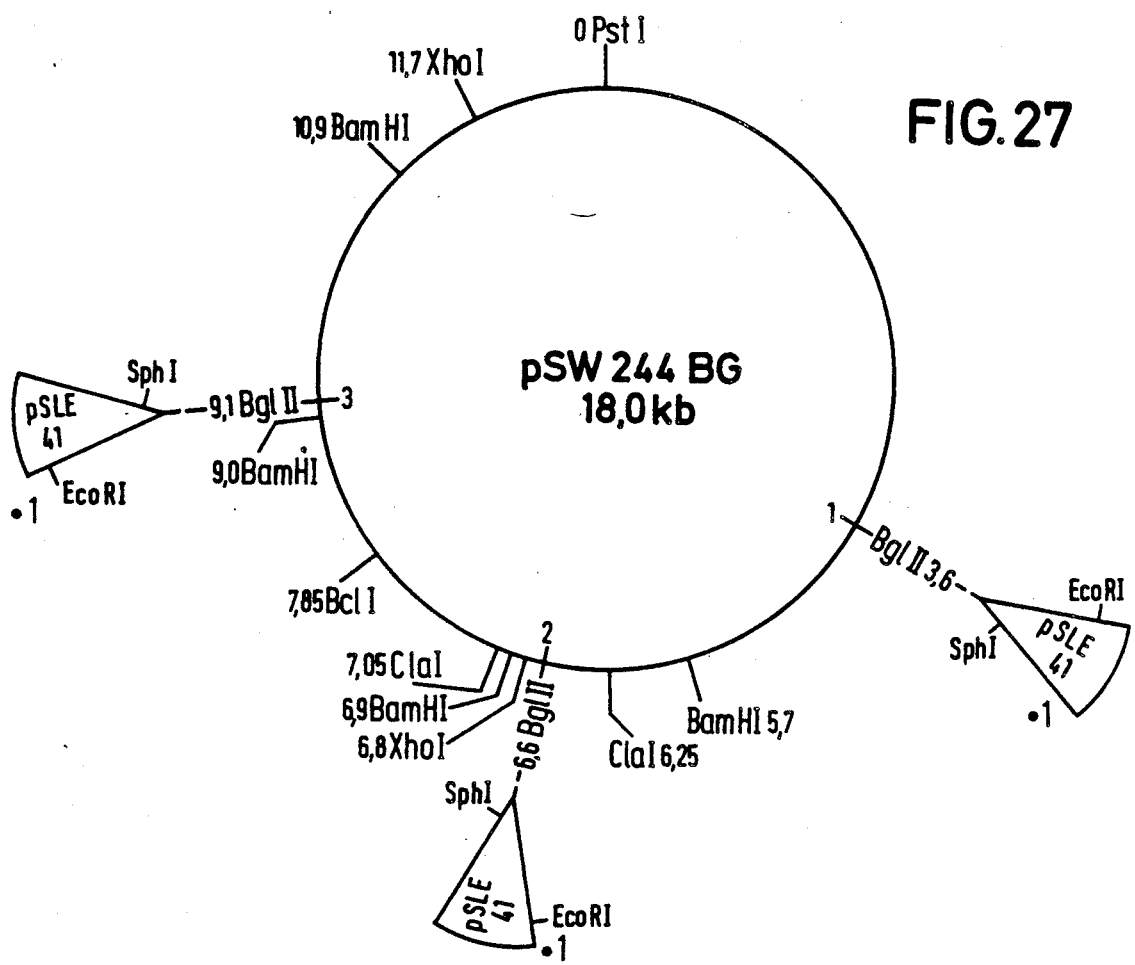
FIG. 27 is a restriction map of pSW 244BG.
Figure 29:
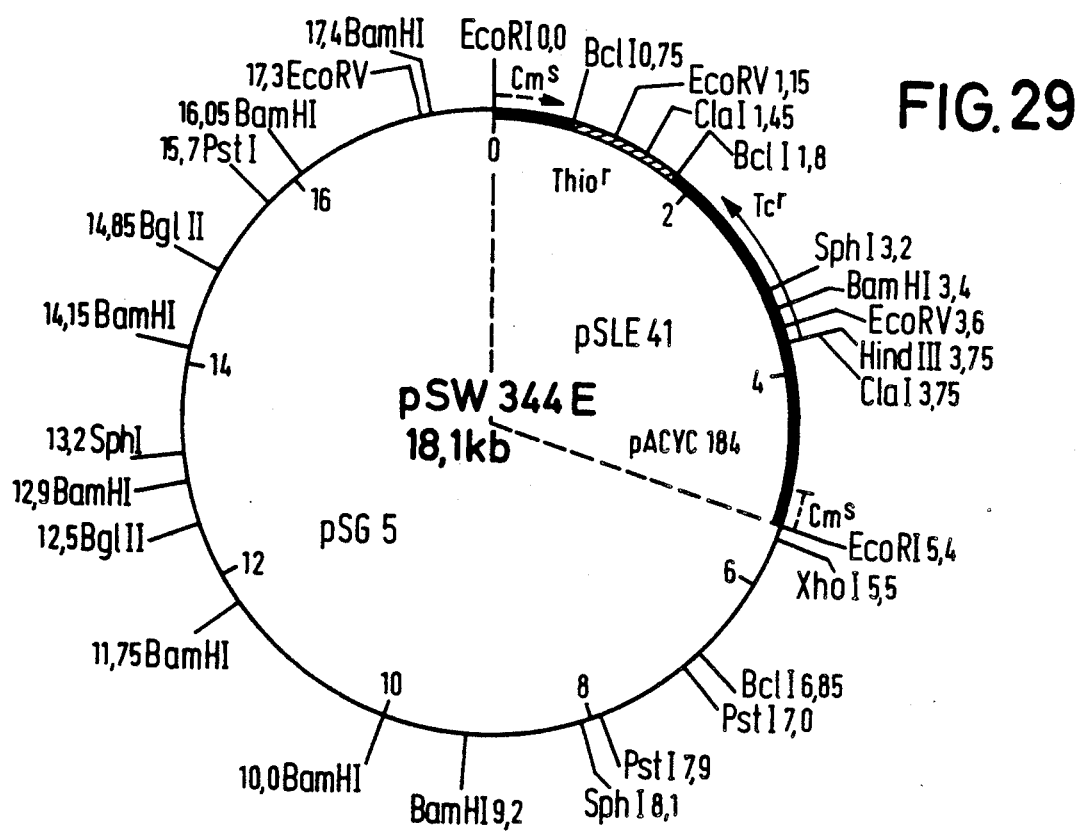
FIG. 29 is a restriction map of pSW 344E.
Figure 30:
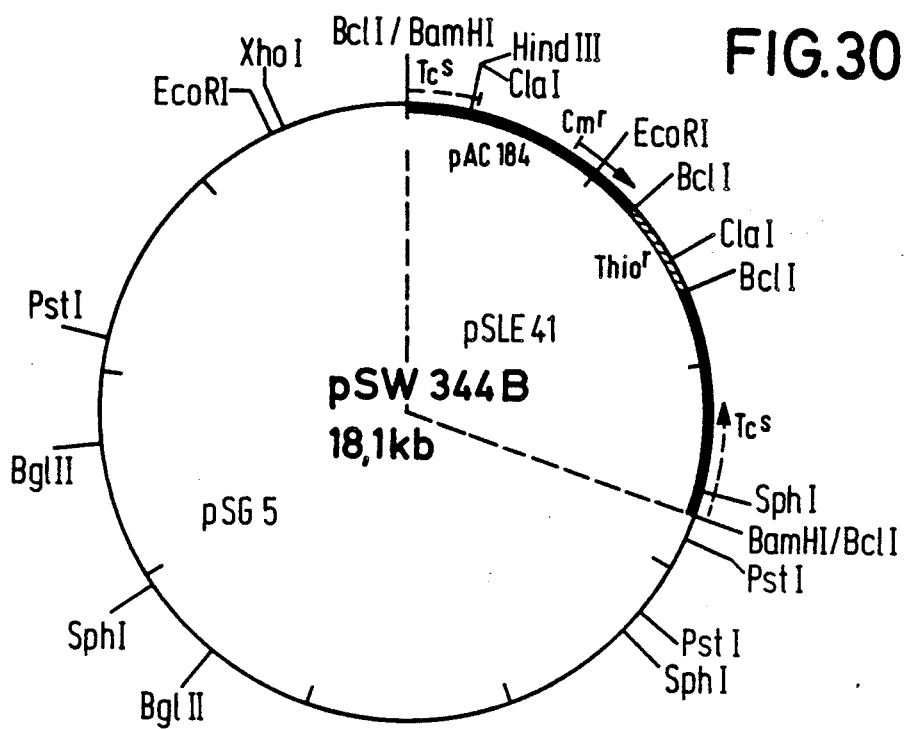
FIG. 30 is a restriction map of pSW 344B.

Particularly preferred shuttle vectors are the plasmids of FIGS. 25 and 27, in each case especially those variants in which the insert pSLE41 is designated by the number 1(FIG. 27a), and the plasmids in FIGS. 26, 28 and 29.

Figure 1:
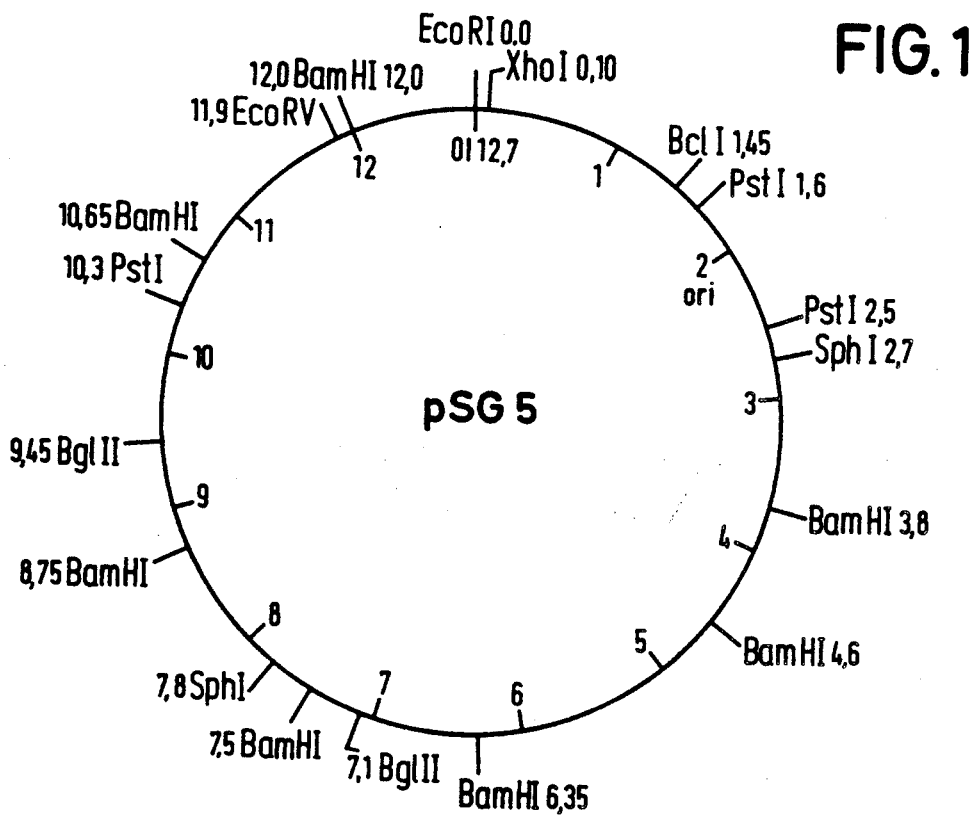
FIG. 1 is a restriction map of pSG 5.
Figure 3:
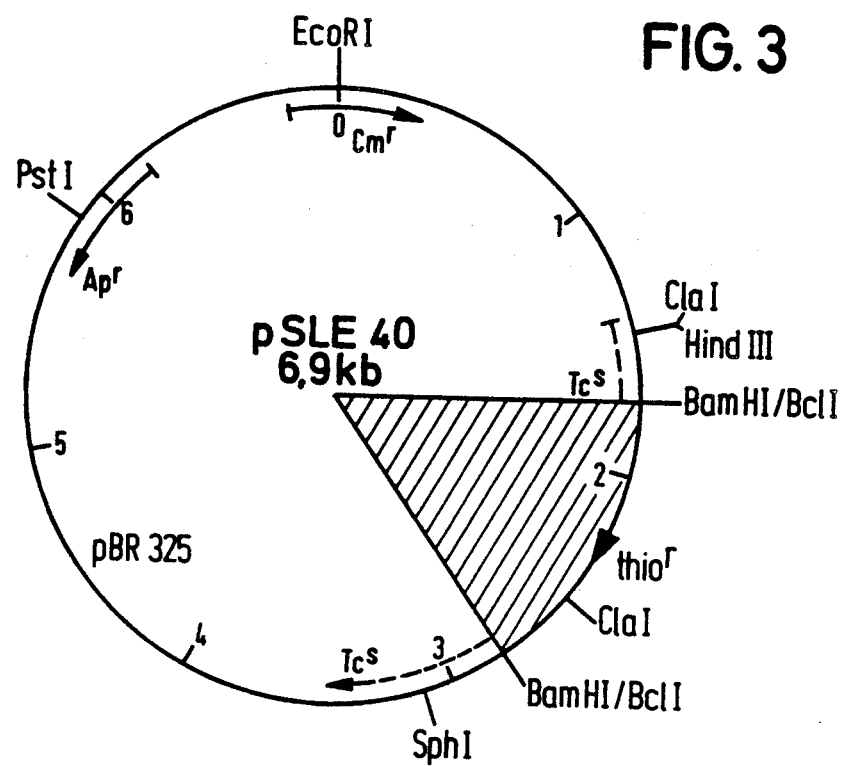
FIG. 3 is a restriction map of pSLE 40.
Figure 2A:
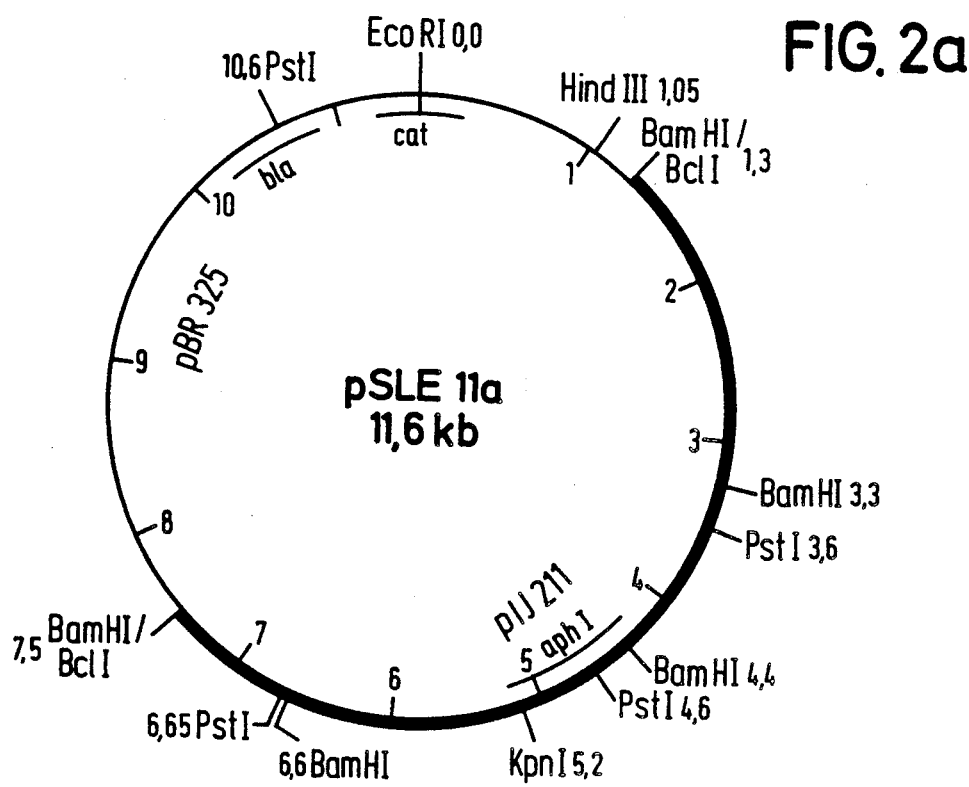
Figure 2B:
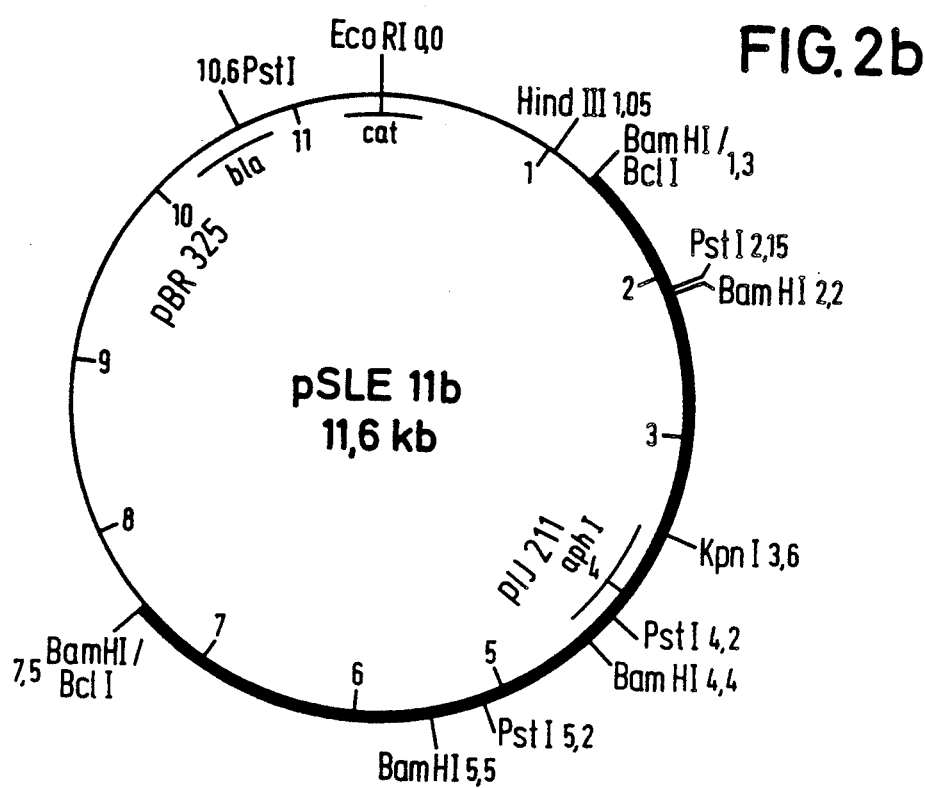
FIG. 2b is a restriction of pSLE 11b.
Figure 4:
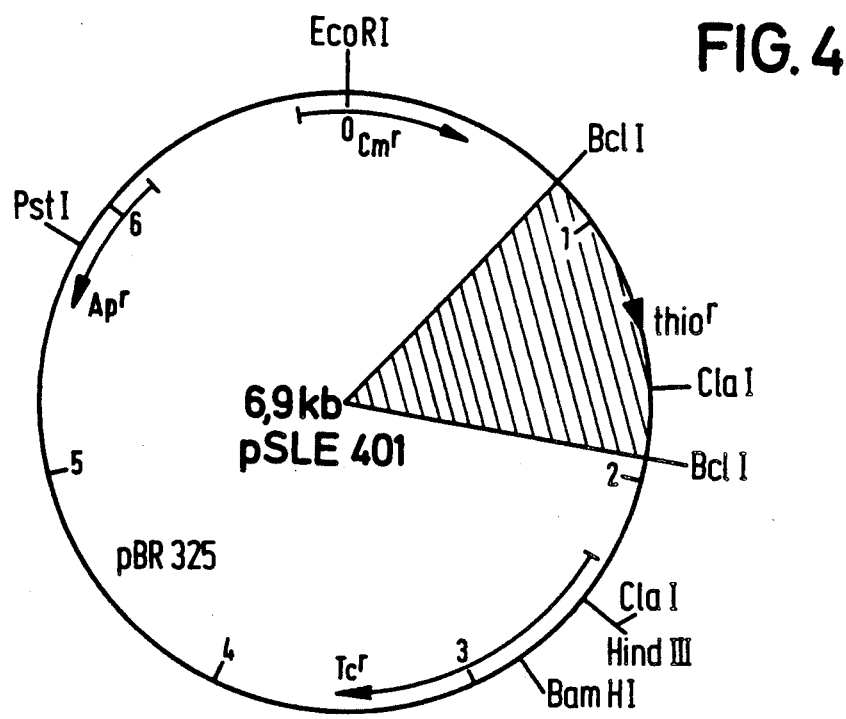
FIG. 4 is a restriction map of pSLE 401.
Figure 5:
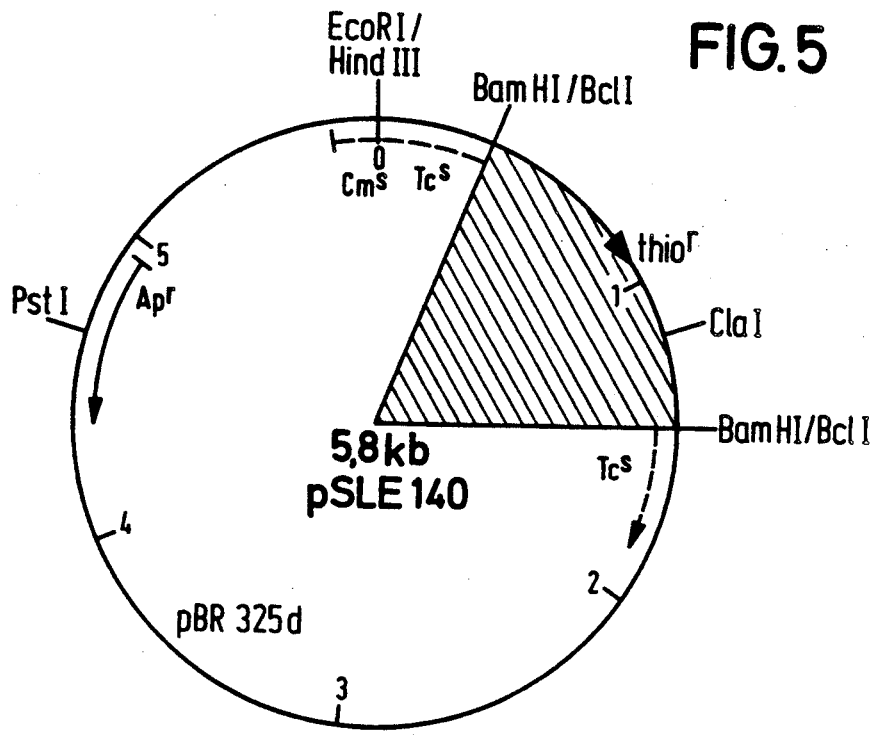
FIG. 5 is a restriction map of pSLE 140.
Figure 6:
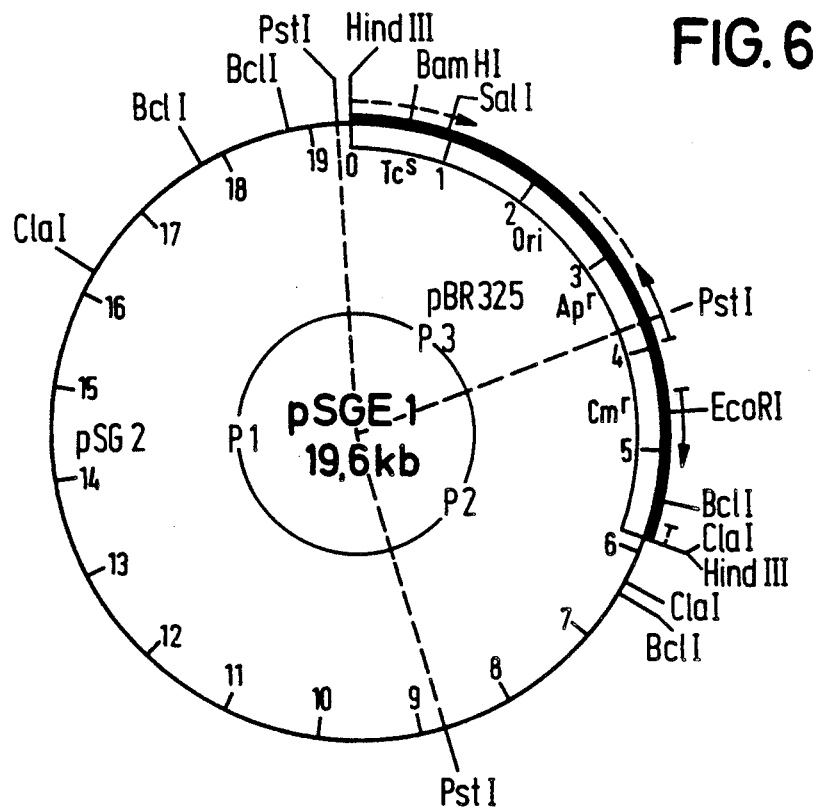
FIG. 6 is a restriction map of pSGE 1.
Figure 7:
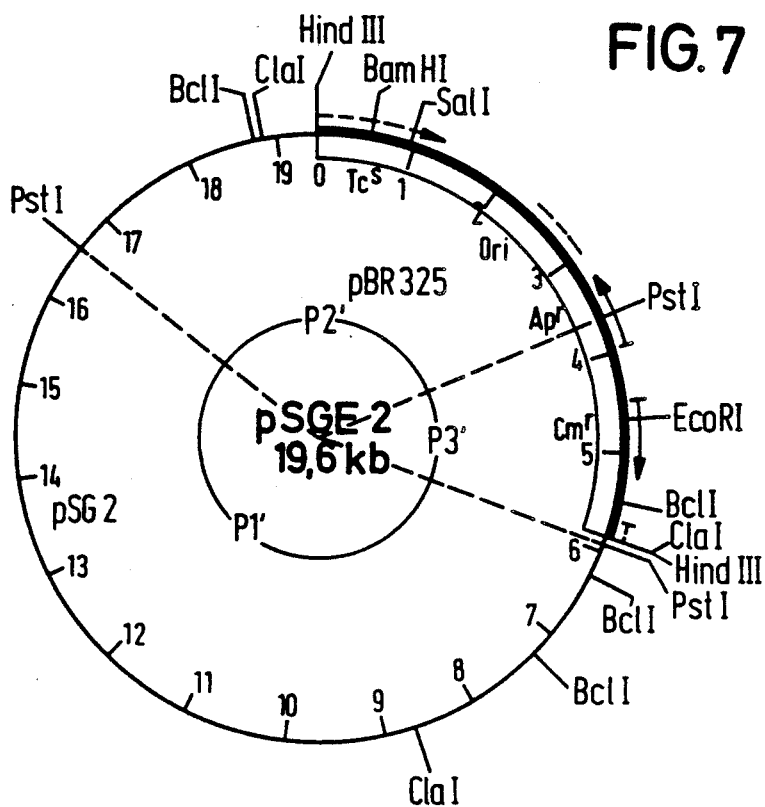
FIG. 7 is a restriction map of pSGE 2.
Figure 8:
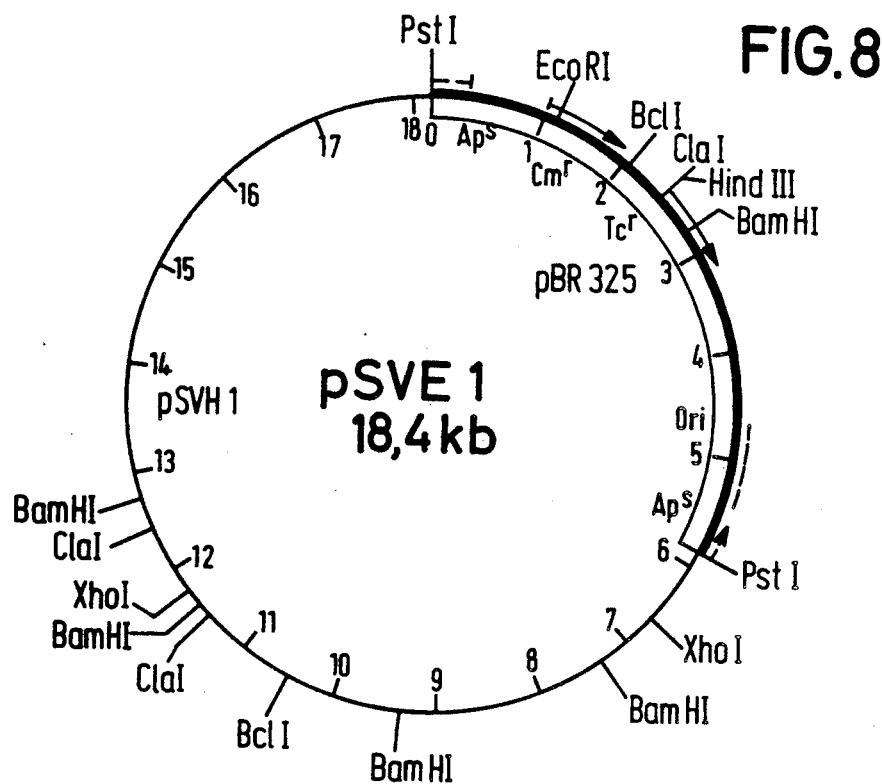
FIG. 8 is a restriction map of pSVE 1.
Figure 9:
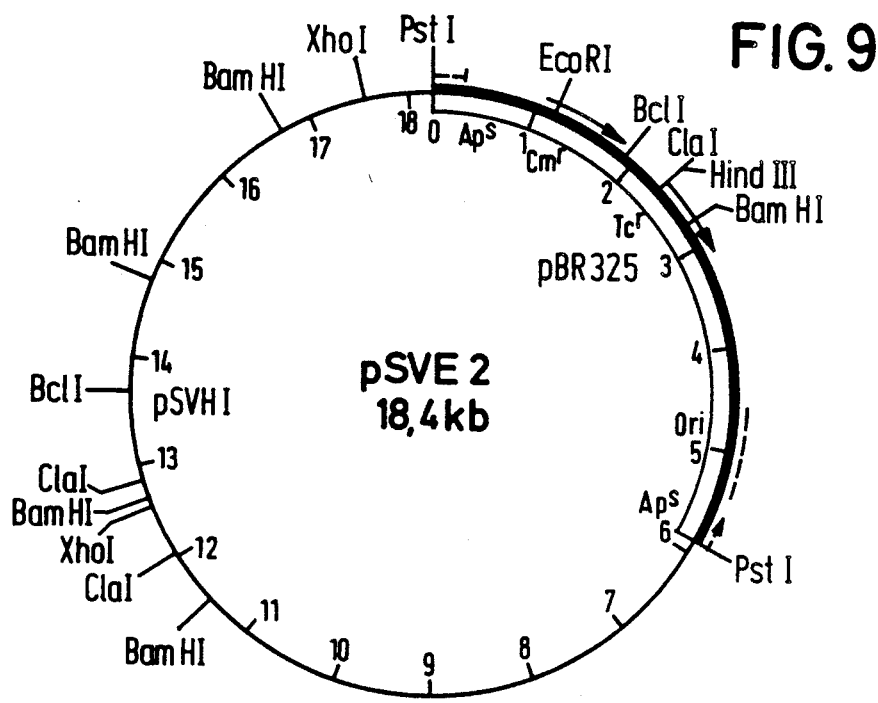
FIG. 9 is a restriction map of pSVE 2.
Figure 10:
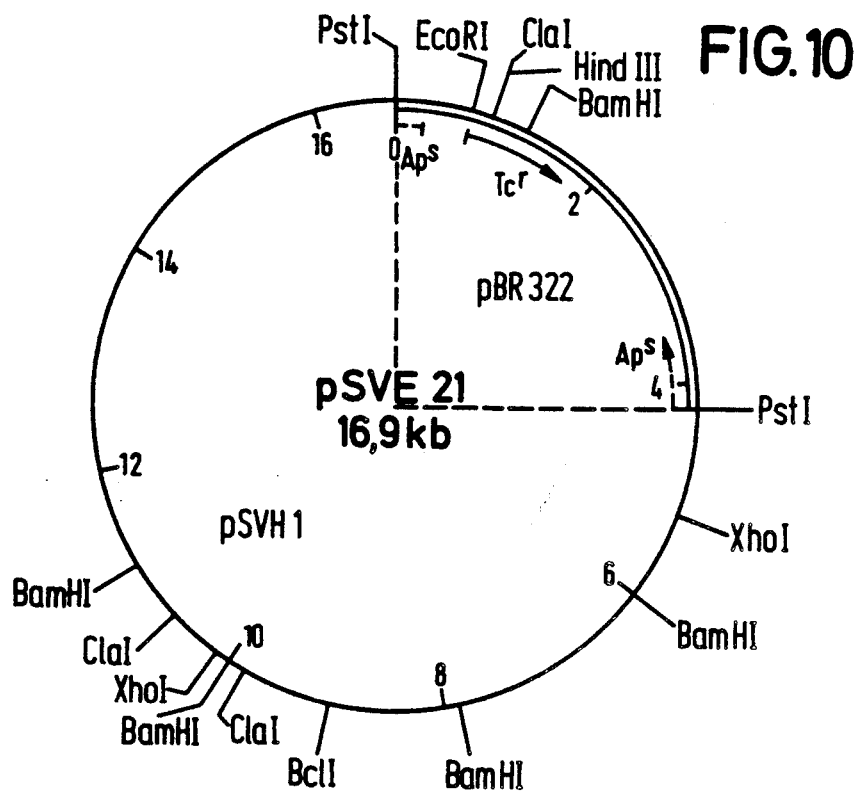
FIG. 10 is a restriction map of pSVE 21.
Figure 11:
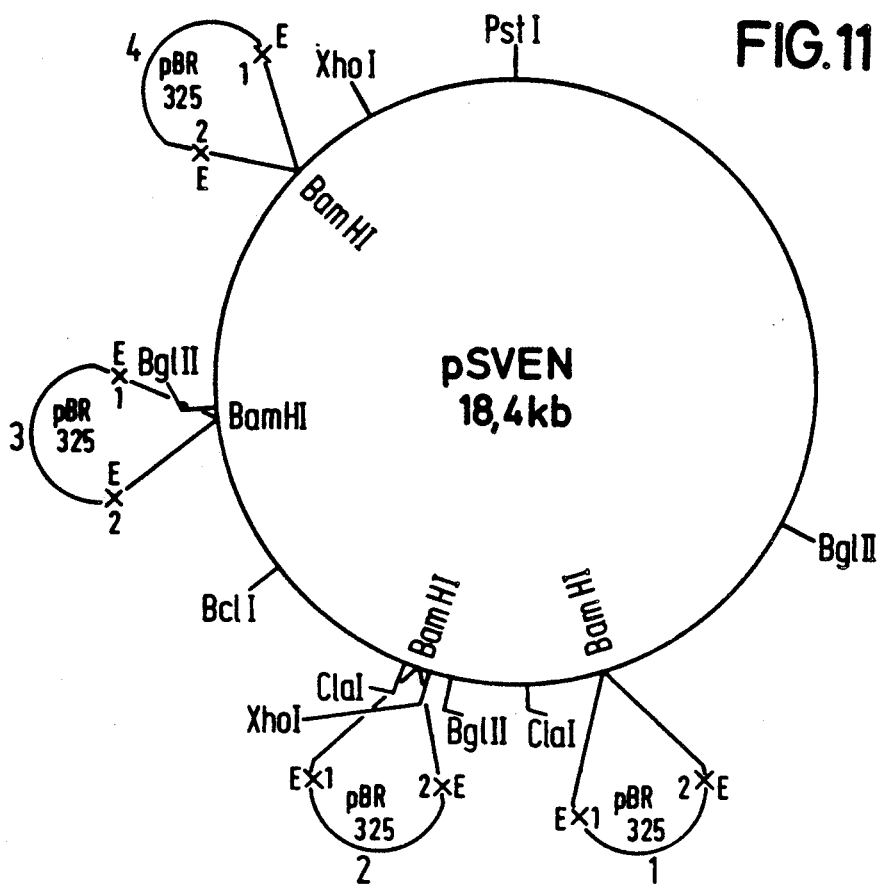
FIG. 11 is a restriction map of pSVEN.
Figure 12:
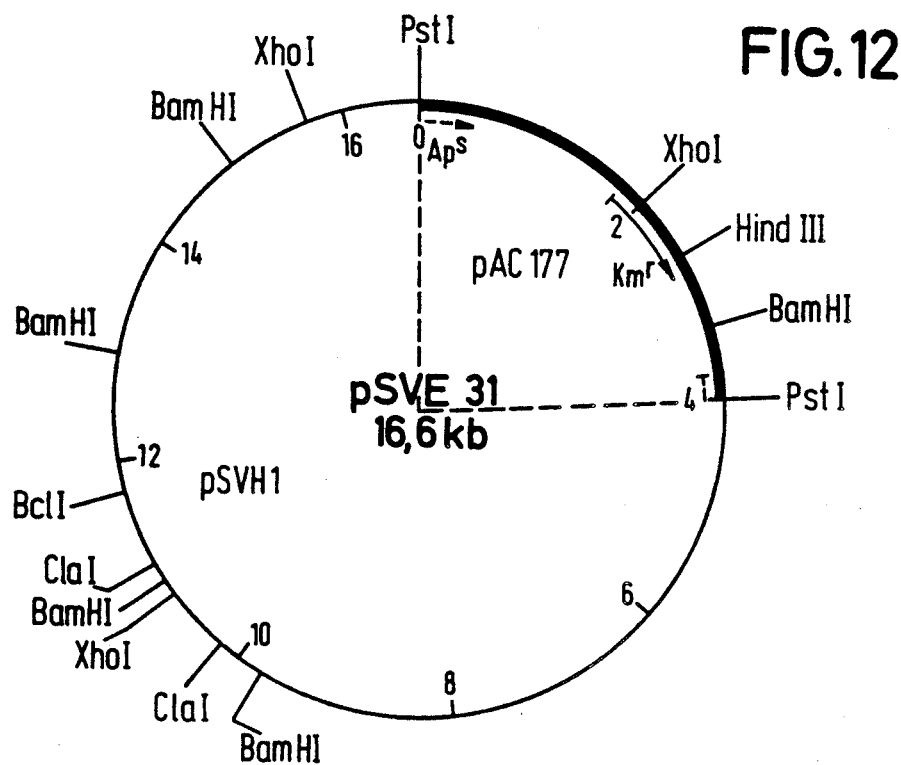
FIG. 12 is a restriction map of pSVE 31.
Figure 13:
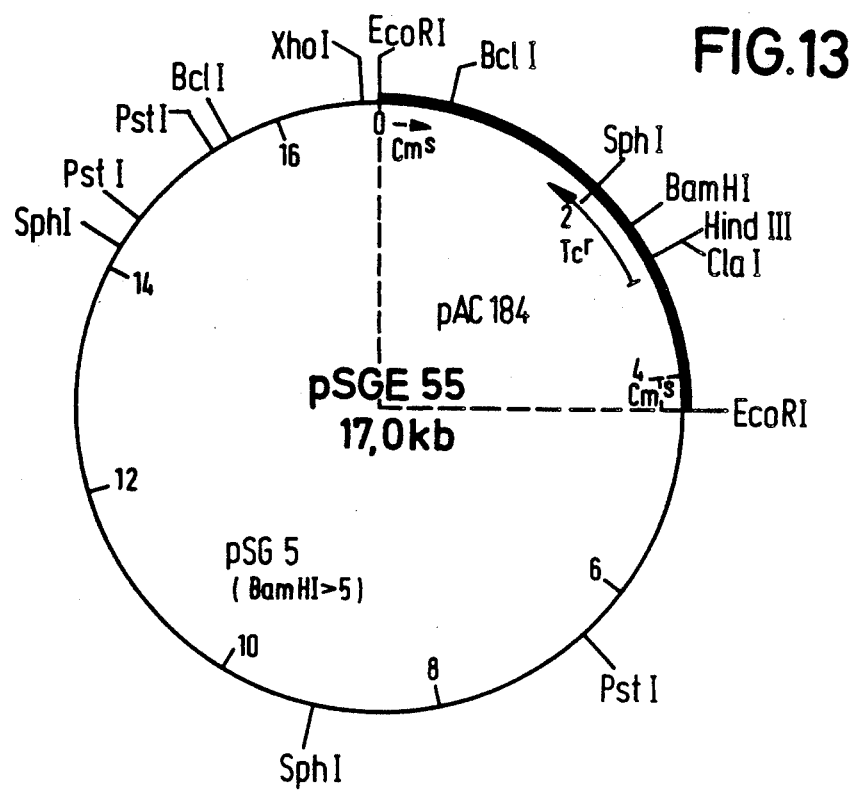
FIG. 13 is a restriction map of pSGE 55.
Figure 14:
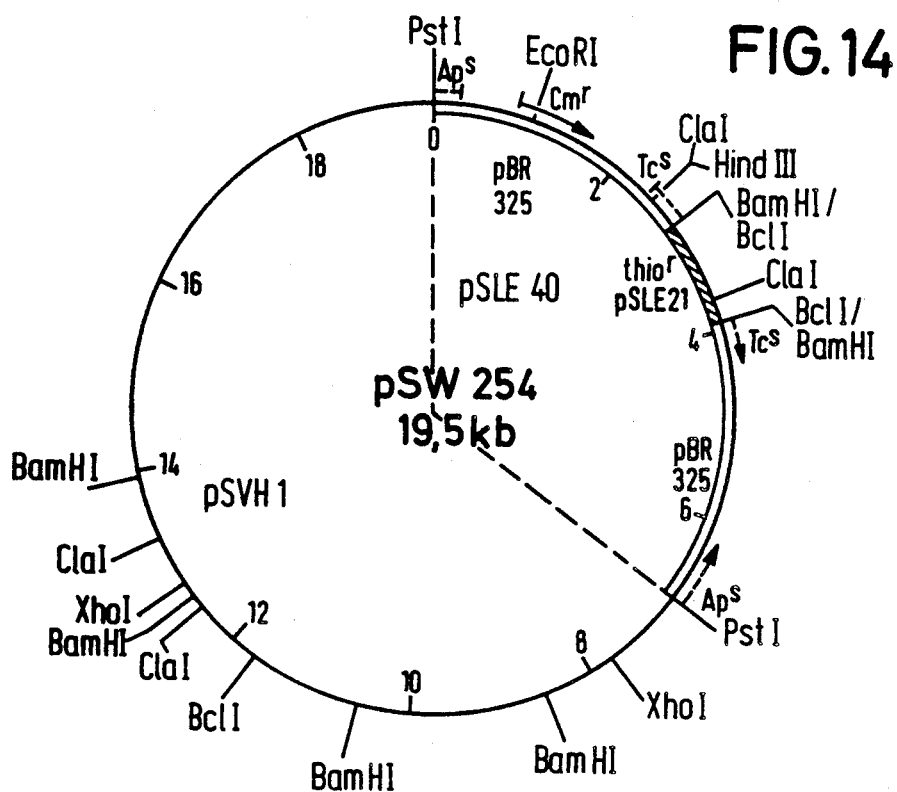
FIG. 14 is a restriction map of pSW 254.
Figure 16:
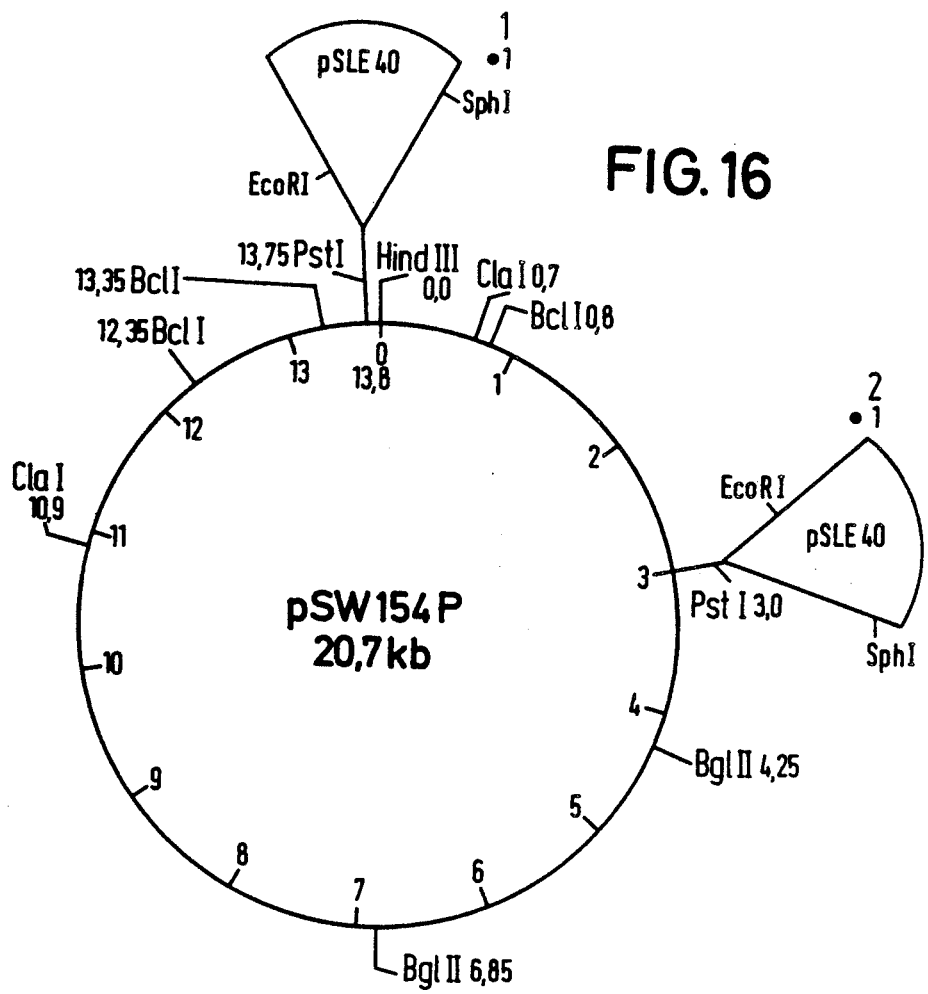
FIG. 16 is a restriction map of pSW 154P.
Figure 15A:
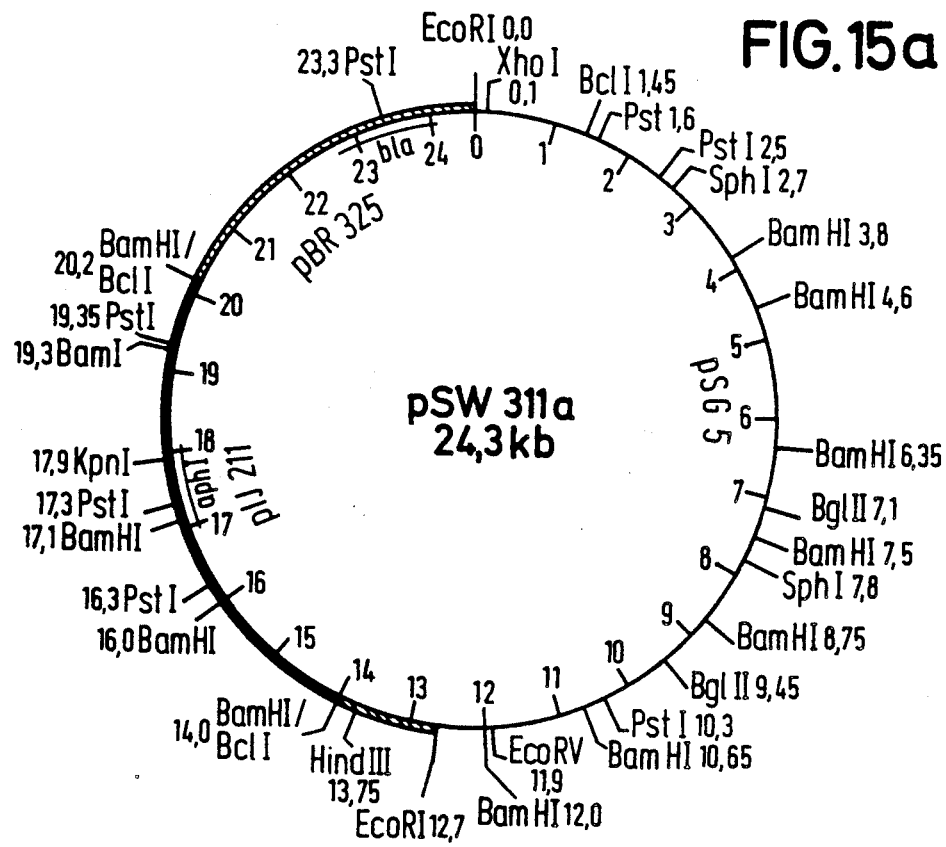
Figure 15B:
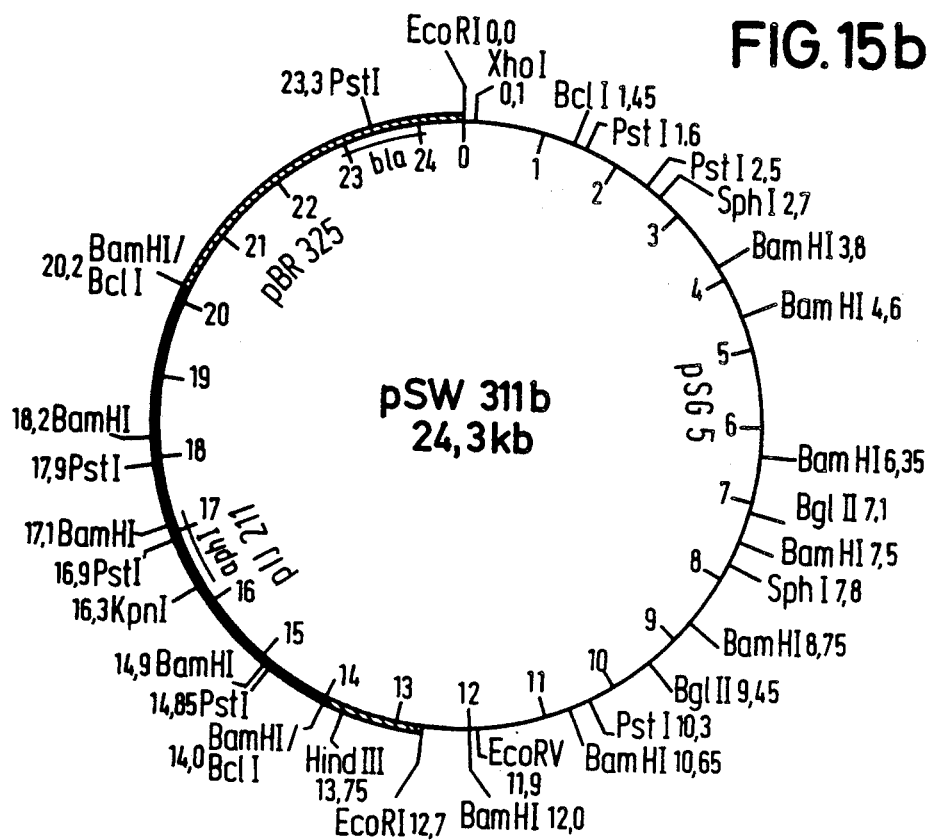
FIG. 15b is a restriction map of pSW 311b.
Figure 17:
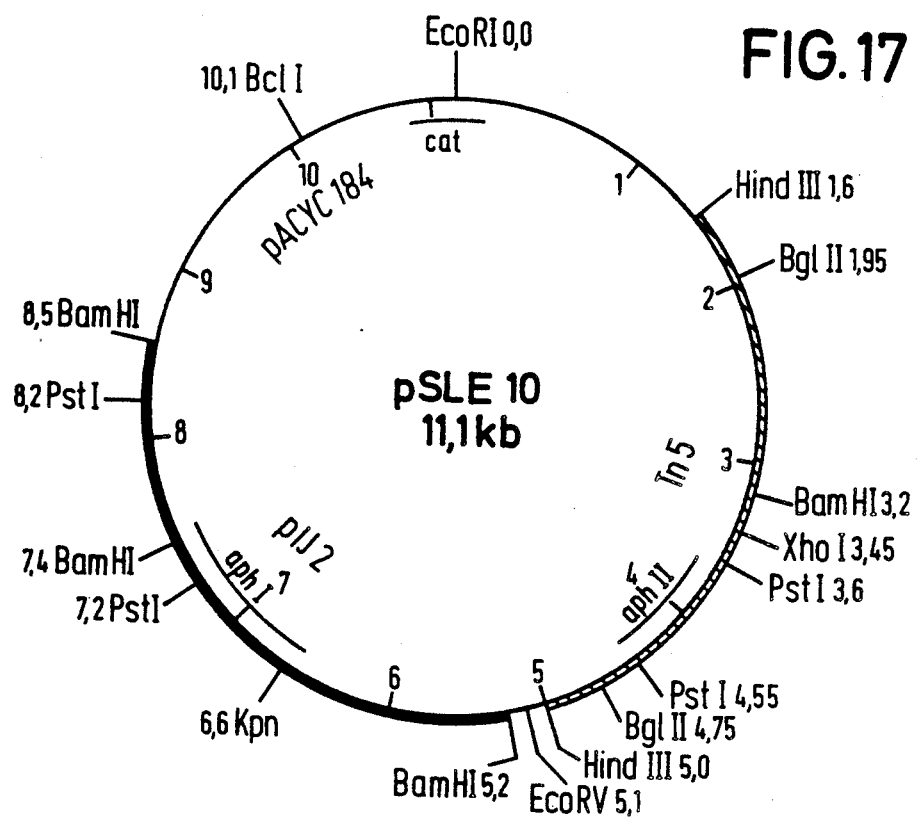
FIG. 17 is a restriction map of pSLE 10.
Figure 18:
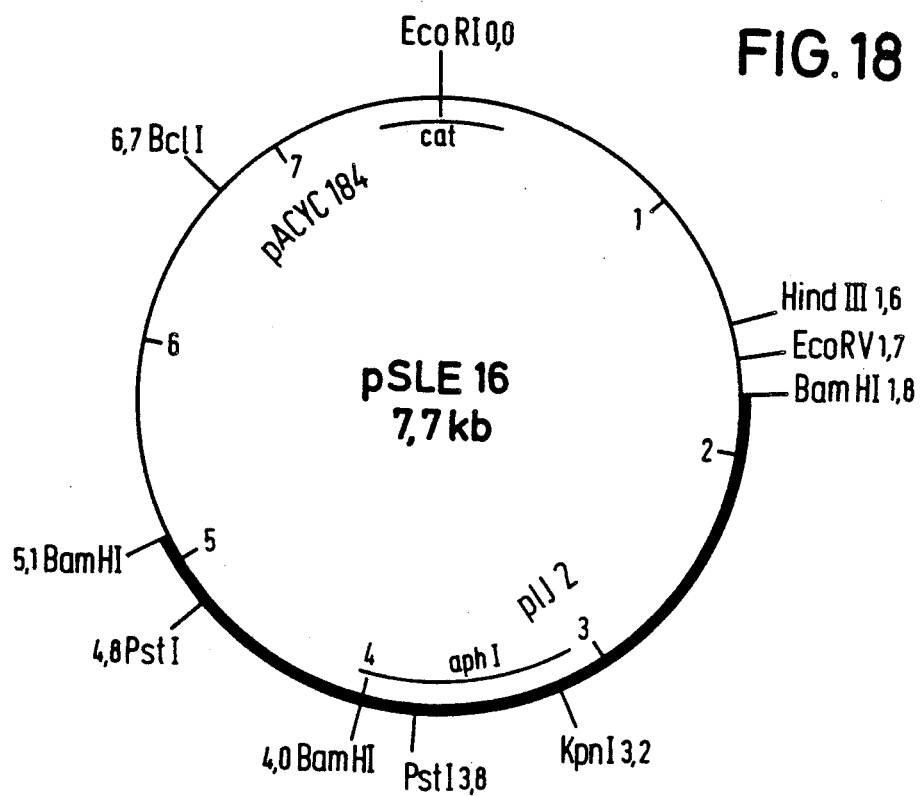
FIG. 18 is a restriction map of pSLE 16.
Figure 19:
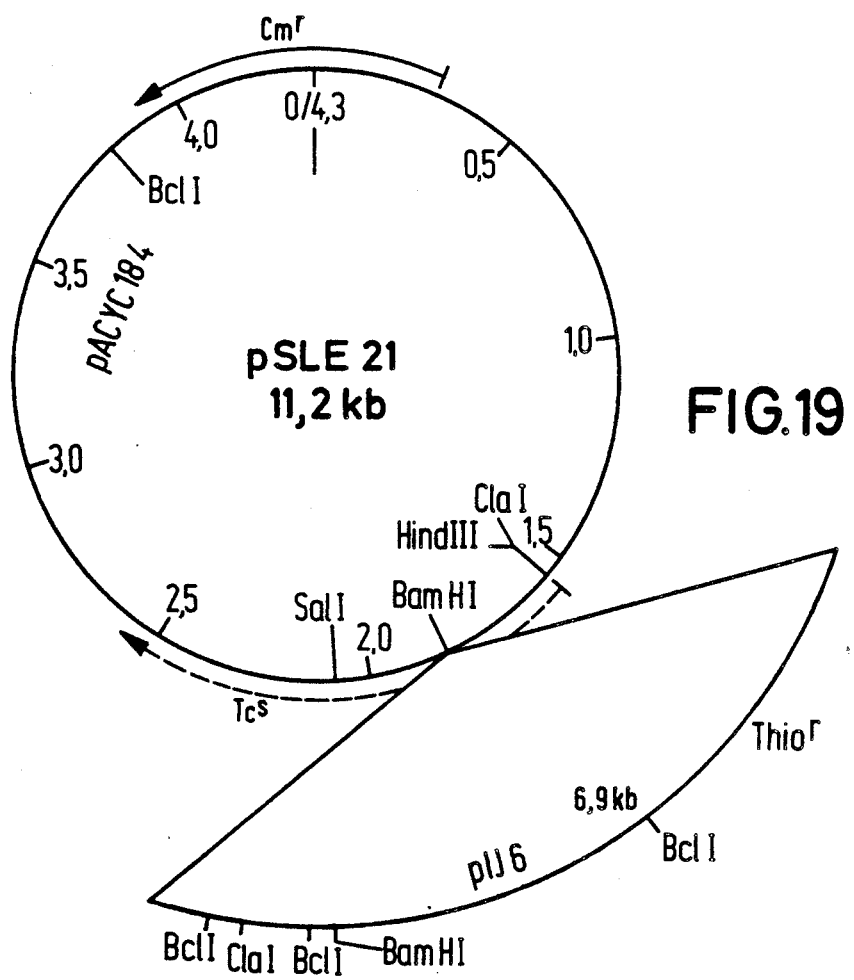
FIG. 19 is a restriction map of pSLE 21.

Of course, it is also possible to modify the Streptomycetes plasmid contribution to the vectors according to the invention by, for example, elimination of non-essential regions. Thus, it has been found that the replication region is located in plasmid pSG5 on the largest BamHI fragment (4.45 kb), namely in the 1 to 3 kb region as shown in FIG. 1. Thus, this "essential region" suffices for the construction of vectors which replicate in Streptomycetes.

The 4.45 kb-long BamHI fragment mentioned, for example, is suitable for the construction of a "minimal replicon". When this fragment is circularized, then the plasmid obtained is distinguished by unique restriction sites for BclI, SphI, BamHI, EcoRI and XhoI. It has been shown for the latter four restriction sites that they are available for cloning. Moreover, on this fragment are also located restriction sites for PvuII (at 12.6, 3.2 and 3.6 kb as shown in FIG. 1), which are located outside the "essential region" and thus are available for cloning or further shortening. Furthermore, restriction sites for SstII (at 0.6, 1.8 and 3.65 kg as shown in FIG. 1) have been found, and the middle one of these is presumably located in the "essential region". In addition, at least five SalI restriction sites are present.

Figure 20:
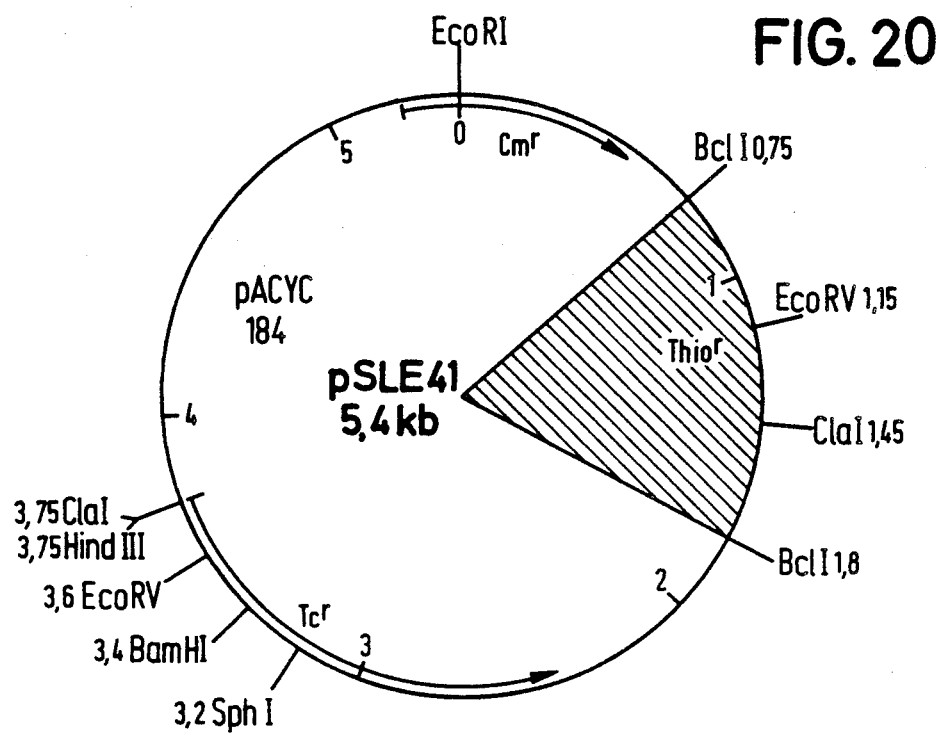
FIG. 20 is a restriction map of pSLE 41.
Figure 21A:
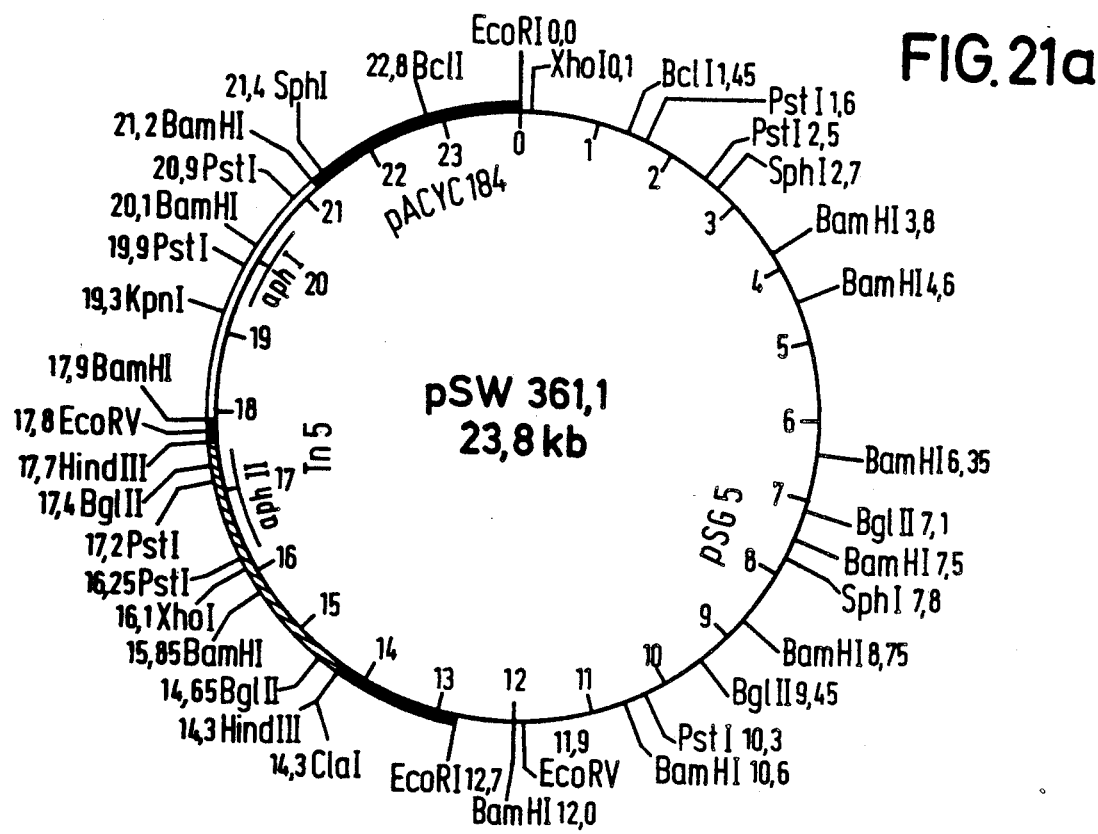
FIG. 21a is a restriction of map of pSW 361.1.
Figure 21B:
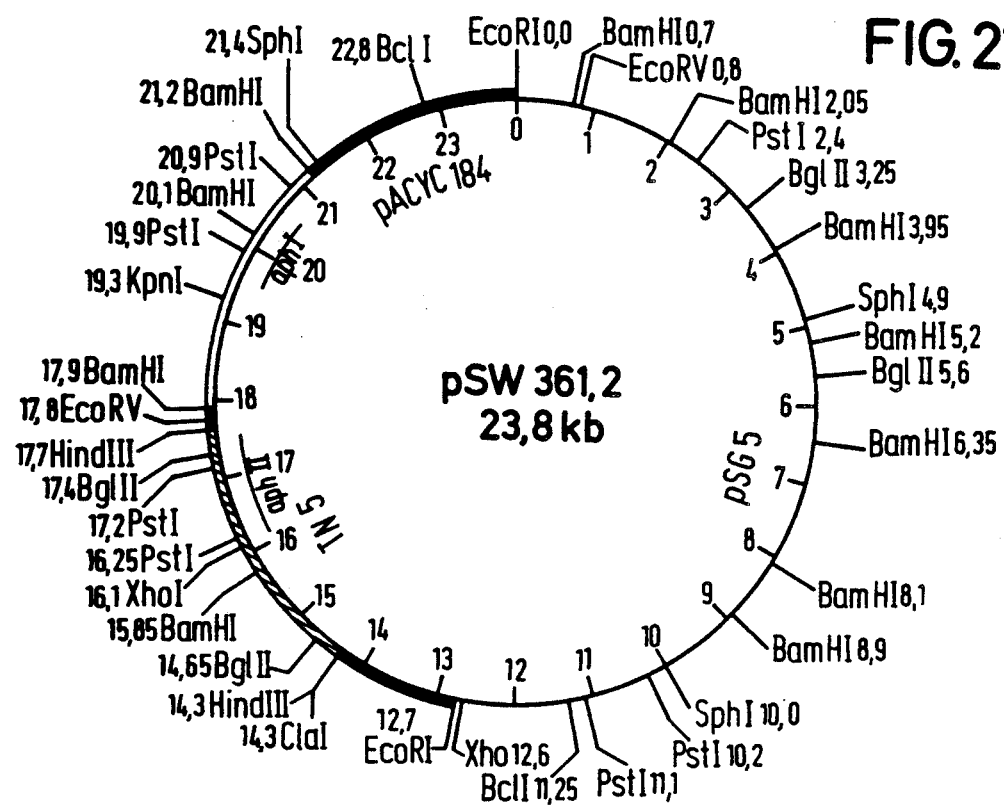
FIG. 21b is a restriction map of pSW 361.2.
Figure 22:
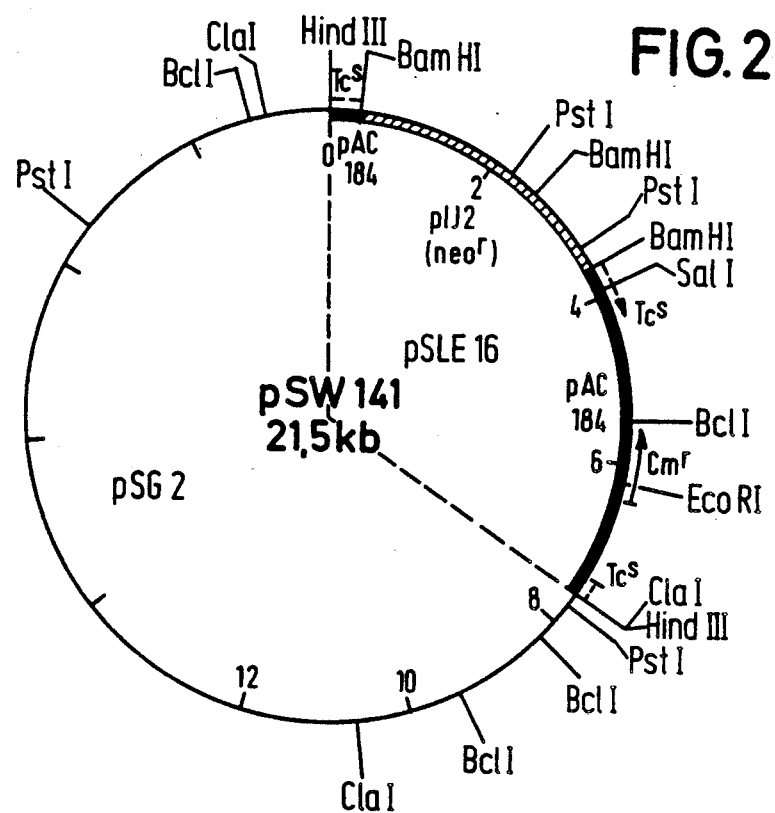
FIG. 22 is a restriction map of pSW 141.
Figure 23:
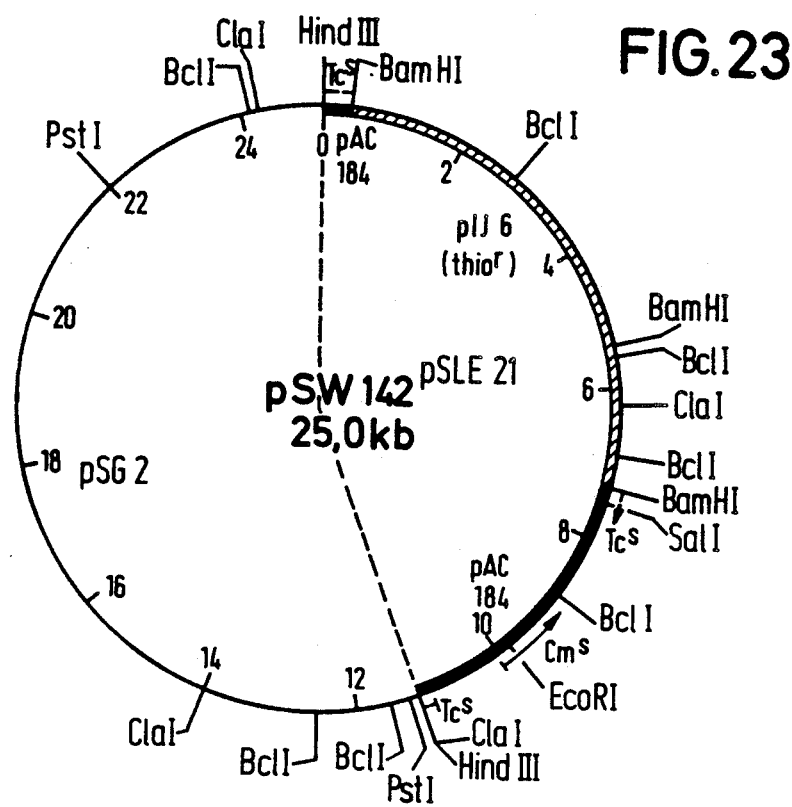
FIG. 23 is a restriction map of pSW 142.
Figure 24:
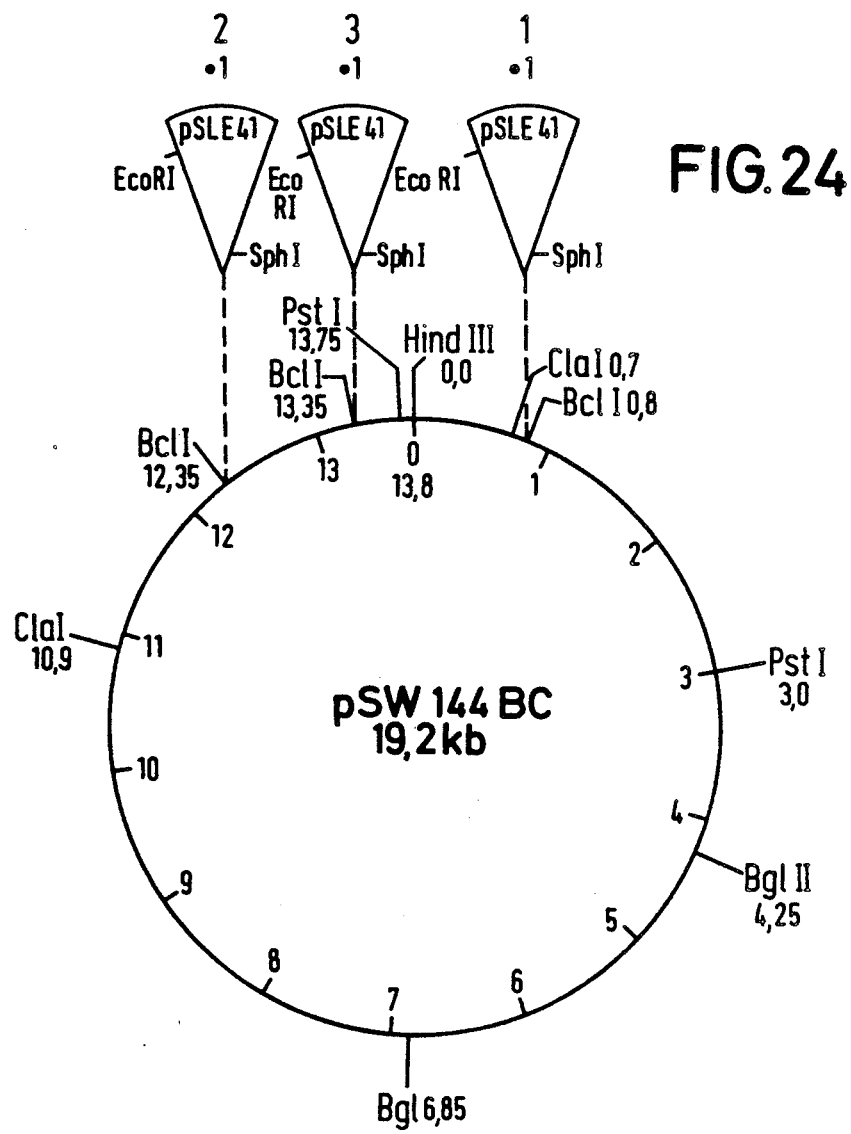
FIG. 24 is a restriction map of pSW 144BC.
Figure 31:
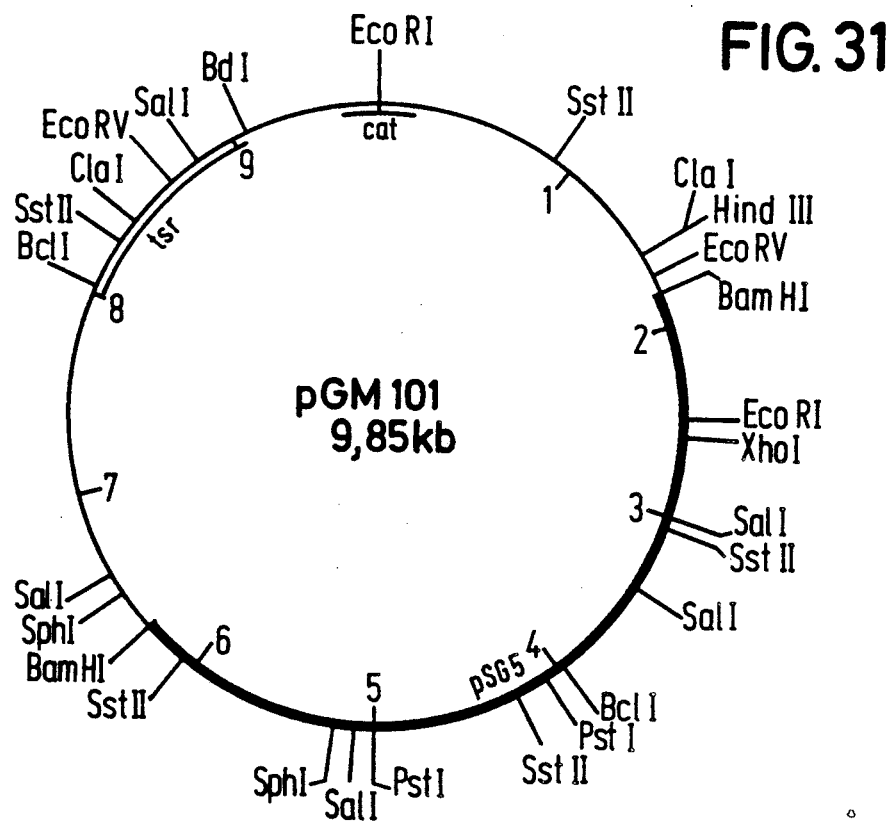
FIG. 31 is a restriction map of pGM 101.

If, for example, the plasmid pSLE41 (FIG. 20) is opened with BamHI and ligated with the 4.45 kb BamHI fragment of pSG5, then the result is the hybrid plasmid pBM101 (FIG. 31, in which only three SalI restriction sites are mapped in the replicon). This plasmid has, inter alia, unique restriction sites for HindIII and XhoI in non-essential regions. The selection markers available are for chloramphenicol resistance (in *E. coli*) and thiostrepton resistance (in Streptomyces). The molecule is 9.9 kb in size.

Figure 32:
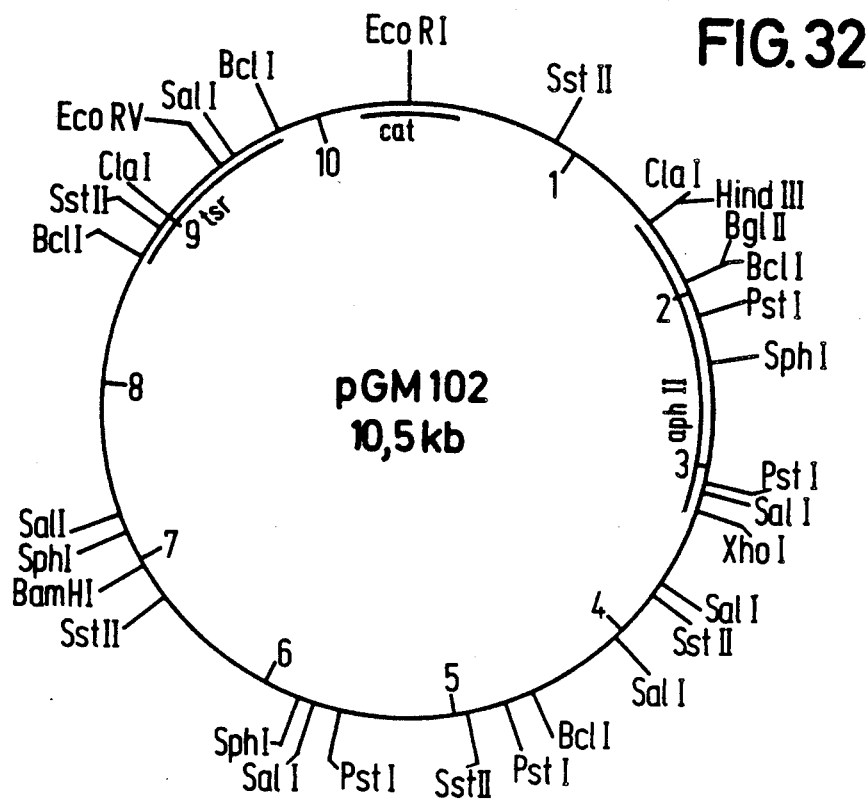
FIG. 32 is a restriction map of pGM 102.

If the 1 kb HindIII-XhoI fragment is eliminated from pGM101, and in its place the 1.6 kb HindIII-XhoII fragment from Tn5, which carries the aphII resistance gene for neomycin, is inserted, then the hybrid plasmid pGM102 is produced (FIG. 32, in which only three SalI restriction sites are mapped in the replicon). The latter replicates in *E. coli* and *S. lividans*. Resistance to chloramphenicol and neomycin are available for selection in *E. coli*, and resistance to thiostrepton and neomycin are available for selection in *S. lividans*. It is possible to use for cloning in *E. coli* the unique restriction sites for EcoRI (inactivation of chloramphenicol resistance) and BglII (inactivation of neomycin resistance), and in Streptomycetes those for EcoRV (inactivation of theiostrepton resistance) as well as BglII, in addition the unique restriction sites for HindIII and XhoI.

The shuttle vectors, according to the invention, having a pAC replicon are stable in *E. coli* in every case. No deletions in the Streptomycetes plasmid portion in *E. coli* have been observed. The vectors (in particular pSW344E, pSW1 and pSW244BG) which have been thoroughly tested in Streptomyces species are stable in the strain investigated (inter alia *S. lividans, S geysirensis, S. ghanaensis* and *S. venezuelae*), and they express the Streptomycetes resistance genes.

The crucial advantages of these vectors are:
1. The host range includes strains (for example *S. ghanaensis*) which cannot be transformed by vectors hitherto known.
2. The copy number is about 10 which is an order of magnitude which is not covered by the vectors hitherto known. The copy numbers reported for other streptomycetes plasmids and their derivatives are 1 (SCP2*, European Patent Application with the Publication No. 92,388), 3–5 (SLP1.2) and 20 copies/cell (for example for pIJ101 and other Kieser, loc. cit.).
3. The plasmids pSVH1, pSG2 and pSG5 and their derivatives belong to different compatibility classes. Moreover, they are compatible with pIJ101 and SLP1.2 replicons. Thus, it is possible to investigate in parallel different genes for various replicons in a cell, in each case in the selected copy number.

Because of their advantageous properties, the shuttle vectors according to the invention are suitable not only for the investigation of genes and for the mapping of replicons (for example by transposon mutagenesis in *E. coli*), but also for the modification and transfer of genes. The procedure is generally known and is described in, for example, the abovementioned patent documents, U.S. Pat. Nos. 4,332,900, 4,338,400, 4,340,674, 4,343,906, 4,362,816, 4,362,817, 4,393,137 and 4,401,761, and in the textbook by Maniatis et al., Molecular Cloning, Cold Spring Harbor 1982. Thus the invention also relates to the use of the shuttle vectors according to the invention for the expression of foreign genes in Streptomycetes.

DETAILED DESCRIPTION OF PREFERRED EMBODIMENTS

The invention is illustrated in detail in the examples which follow.

First the isolation of the plasmid pSG5 is described:

The following media are suitable for cultivation of the strain S. ghanaensis DSM 2932 for subsequent lysis:

| Lysis medium A | | Lysis Medium B | | Lysis Medium C | |
| --- | --- | --- | --- | --- | --- |
| glucose | 10 g | yeast extr. | 3 g | casein-peptone | 30 g |
| peptone | 4 g | peptone | 5 g | soymeal- | |
| yeast extr. | 4 g | malt extr. | 3 g | peptone broth | |
| KH$_2$PO$_4$ | 2 g | glucose | 10 g | (Merck 5459) | |
| K$_2$HPO$_4$ | 4 g | sucrose | 340 g | glycine | 10 g |
| MgSO$_4$ | 0.5 g | glycine | 5 g | H$_2$O | 1 l |
| glycine | 10 g | MgCl$_2$.6H$_2$O | 1 g | | |
| H$_2$O | 1 l | H$_2$O | 1 l | | |

About 100 m of nutrient medium in a 500 ml conical flask are inoculated with a homogenized single colony and incubated at 30° C. in an orbital shaker (120 rpm) for 2-3 days.

About 50 ml of a 3 day-old, homogenized liquid culture are harvested in JA-20 tubes in a Beckman J21C cooled centrifuge (10 min, 10000 rpm, 25° C.) and washed once in TESu (10 mM tris HCl, 1 mM EDTA (pH 8), 10% sucrose). 2 g of cells are resuspended in 5 ml of lysozyme solution (0.3 M sucrose, 25 mM tris HCl (ph 8), 25 mM EDTA (pH 8), 4 mg/ml lysozyme) and incubated at 37° C. in an orbital shaker (100 rpm). After 30-45 min, the cells have been converted into protoplasts. The breakdown of the cell membrane and denaturation of the DNA is carried out by addition of 2.5 ml of lysis mix (0.3 M NaOH, 2% sodium dodecyl sulfate) and immediate vigorous mixing. Heat treatment for 10 minutes (70° C.) completes the lysis and denaturation. 800 μl of acid phenol/chloroform solution are added at room temperature (preparation of the acid phenol/chloroform solution: mix 500 ml of chloroform, 200 ml of H$_2$O, 500 g of phenol and 0.5 g of hydroxyquinoline and use the lower phase), in order to denature the proteins and renature the DNA. The mixture is thoroughly mixed in a shaker (®VORTEX) for about 20 sec, and then pelleted in a cooled centrifuge (15 min, 12000 rpm 4° C.).

7 ml of the plasmid-containing supernatant are then further purified in an ultranecentrifuge: 7 g of CsCl, 7 ml of lysate and 0.2 ml of ethidium bromide solution (30 mg/ml) are mixed and centrifuged in an ultracentrifuge (®KONTRON TGA50) at 34000 rpm (20° C.) for 48 h. The plasmid band is visualized via its fluorescence on UV irradiation and is removed using a syringe. The solution is decolorized and dialyzed and is then ready for further investigations. It contains about 1 μg of plasmid DNA per 20 μl of solution.

EXAMPLE 1

Preparation of the plasmid pSLE40 (as an example of a modified plasmid of the pBR series)

pBR325 DNA can be obtained from plasmid bearing cells by known processes (Maniatis et al.). The plasmid pIJ6 can be isolated from Streptomyces lividans TC14 using the known Streptomycetes techniques (see isolation of pSG5, pSG2 or, for example, Thompson et al., Nature 286 (1980) 525 or U.S. Pat. No. 4,360,597).

For the cloning, the plasmid pBR325 is linearized using the restriction enzyme BamHI. 1 μg of DNA is incubated in cleavage buffer (50 nM tris HCl, pH 8.0, 10 mM MgCl$_2$, 50 mM NaCl) in the presence of 1 unit of BamHI (manufactured by BRL, Neu-Isenburg) at 37° C. for 1 h. The reaction is stopped by phenol treatment (Maniatis et al.) and the DNA is purified by ethanol precipitation. To obtain the DNA fragment which carries the thiostrepton resistance, pIJ6 DNA is cut with BclI (procedure as above with the change that BclI replaces BamHI, incubation at 50° C. instead of 37° C.). Subsequent treatment of pBR325 with alkaline phosphatase (from calf intestine, manufactured by Boehringer Mannheim) removes the 5'-phosphate ends of the DNA and prevents the religation of pBR325 (Maniatis et al.). The two DNA samples (in cleavage buffer) are mixed (0.1 μof pBR325 and 1 μg of pIJ6) and heated to 70° C. in order to open H bridges. The reaction conditions are set up by addition of mercaptoethanol (final concentration 10 mM) and ATP (0.1 mM). The DNA is incubated in the presence of 1 unit of T4 DNA ligase (Boehringer Mannheim) at 4° C. for 12 h. E. coli is transformed with the DNA mixture (Maniatis et al.), and the cells are selected for chloramphenicol resistance and tetracycline sensitivity.

Individual colonies are subjected to rapid lysis (T. Eckhardt, Plasmid 1 (1978) 584) to determine the plasmid sizes. It is known that the thiostrepton-resistance gene is located on a 1. kb-long BclI fragment of the pIJ6 plasmid (kieser et al., Mol. Gen. Genet. 185 (1982) 223); ie. a plasmid 6.9 kb in size (pBR325 5.8kb + thiostrepton resistance gene (Thio$^r$) 1.1 kb) is sought in an agarose gel. DNA is isolated (see above) from cells which carry a plasmid of the required length, and restriction analysis is used to elucidate whether the correct DNA fragment has been inserted. The restriction sites of the fragment are known (Kieser et al.), so that success of cloning can be verified.

EXAMPLE 2

Preparation of the Shuttle Vector pSW311

The plasmid pSLE11 can be obtained from E. coli by known processes (Maniatis et al.). The plasmid pSG5 is isolated from S. ghanaensis as described above.

For the cloning, the two plasmids are linearized in parallel using EcoRI. 1 μg of DNA is incubated in cleavage buffer in the presence of 1 unit of EcoRI (manufactured by Boehringer Mannheim) at 37° C. for 1 h. The reaction is stopped by phenol treatment, and the DNA is purified by ethanol precipitation (Maniatis et al.).

pSLE11 DNA is advantageously also treated with alkaline phosphatase in order to suppress religation (Maniatis et al.).

The DNA samples (in cleavage buffer) are then mixed (0.2 μg of pSLE11 and 1 μg of pSG5), heated to 70° C. and the ligase reaction conditions are set up by addition of mercaptoethanol (final concentration 10 mN) and ATP (0.1 mM). The mixture is incubated in the presence of 1 unit of T4 DNA ligase (Boehringer Mannheim) at 4° C. for 12 h.

The mixture is then transformed into E. coli (Maniatis et al.) and selection for colonies with ampicillin resistance and chloramphenicol sensitivity is carried out. Colonies with the appropriate resistance pattern are subjected to rapid lysis for determination of the plasmid sizes. Plasmid DNA is isolated from cells which contain a plasmid of the required length (24.3 kb), and restriction analysis is used to elucidate whether the desired shuttle vector pSW311 is present.

The hybrid plasmids specified in Table 3 can be prepared in an analogous manner.

EXAMPLE 3

Preparation of the Plasmid pSLE41 (as an Example of a Modified Plasmid from the pAC Series)

Construction of pSLE41 pACYC184 DNA can be obtained from plasmid-bearing cells by known processes (Maniatis et al.). However, wild type $E.$ $coli$ cells possess a dam methylase and modify the DNA in such a manner that the necessary restriction with BclI is impossible. Thus, in this case, a dam$^-$mutant of $E.$ $coli$ is used to isolate the DNA.

The plasmid pIJ6 can be isolated from $Streptomyces$ $lividans$ TC14 by the techniques known for Streptomycetes (see above).

For the cloning, the plasmid pACYC184 is linearized using the restriction enzyme BclI.

1 μg of DNA is incubated in cleavage buffer in the presence of 1 unit of BclI (manufactured by BRL, Neu-Isenburg) at 50° C. for 1 h. The reaction is stopped by phenol treatment, and the DNA is purified by ethanol precipitation. Subsequent treatment with alkaline phosphate (from calf intestine, manufactured by Boehringer Mannheim) removes the 5'-phosphate ends of the DNA and prevents the religation of pACYC184. pIJ6 DNA is cut with BclI (for procedure, see above) in order to obtain the DNA fragment which carries the thiostrepton resistance.

The two DNA samples (in cleavage buffer) are mixed (0.1 μg of pACYC184 and 1 μg of pIJ6) and heated to 70° C. in order to open up H bridges. The reaction conditions are set by addition of mercaptoethanol (final concentration 10 mM) and ATP (0.1 mM). The DNA is incubated in the presence of 1 unit of T4 DNA ligase (Boehringer Mannheim) at 4° C. for 12 h.

$E.$ $coli$ is transformed with the DNA mixture (Maniatis et al.) and the cells are selected from resistance to tetracycline and chloramphenicol.

Individual colonies are subjected to rapid lysis to determine the plasmid size. A plasmid of size 5.4 kb (pACYC184 4.3 kb + thio$^r$ 1.1 kb) is sought on an agarose gel. DNA is isolated (see above) from cells which carry a plasmid of the required length, and restriction analysis is used to elucidate whether the correct DNA fragment has been inserted. The restriction sites of the fragment are known (Kieser et al.), so that success of cloning can be verified.

EXAMPLE 4

Preparation of the Plasmid pSW344E

The plasmid pSLE41 can be obtained from $E.$ $coli$ by known processes (Maniatis et al.). The plasmid pSG5 is isolated from $S.$ $ghanaensis$ 2932 as described above.

For the cloning, the two plasmids are linearized in parallel using EcoRI. 1 μg of DNA is incubated in cleavage buffer in the presence of 1 unit of EcoRI (manufactured by Boehringer Mannheim) at 37° C. for 1 h. The reaction is stopped by phenol treatment, and the DNA is purified by ethanol precipitation. pSLE41 DNA is advantageously also treated with alkaline phosphatase in order to suppress religation. The DNA samples (in cleavage buffer) are then mixed (0.2 μof pSLE41 and 1 μg of pSG5), heated to 70° C. and the ligase reaction conditions are set up by addition of mercaptoethanol (final concentration 10 mM) and ATP (0.1 mM). The mixture is incubated in the presence of 1 unit of T4 DNA ligase (Boehringer Mannheim) at 4° C. for 12 h. The mixture is then transformed into $E.$ $coli$ (Maniatis et al.), and colonies having tetracycline resistance and chloramphenicol sensitivity are selected.

Colonies having the appropriate pattern of resistance are subjected to rapid lysis to determine the plasmid sizes. DNA is isolated from cells which contain a plasmid of the required length (18.1 kb), and restriction analysis is used to elucidate whether the DNA provides the appropriate restriction pattern necessary if ligation of pSLE41 and pSG5 has taken place.

The hybrid plasmids specified in Table 5 can be prepared in an analogous manner.

EXAMPLE 5

If the process is carried out as in Example 4, but the "minimal replicon" of pSG5, which has been linearized with BamHI and is described below, is ligated with BamHI-cut pSLE41, then the shuttle vector pGM101 is obtained.

Construction of a minimal replicon from pSG5.

The plasmid pSG5 is isolated from $S.$ $ghanaensis$ DSM 2932 as described above. The plasmids pSLE40 and pSLE41 can be obtained from $E.$ $coli$ by known processes (Maniatis et al.).

Fragments of pSG5 are cloned in pSLE40 or pSLE41, namely the SphI, BamHI and BglII fragments in the SphI, BamHI and BamHI restriction sites of pSLE41, and the PstI fragments in the PstI restriction site of pSLE40. For the cloning, the two plasmids (one of the pSLE plasmids and pSG5) are linearized in parallel using the abovementioned enzymes. The reaction is stopped by phenol treatment, and the DNA is purified by ethanol precipitation (Maniatis et al.).

pSLE40 and pSLE41 DNA is advantageously also treated with alkaline phosphatase in order to suppress religation (Maniatis et al.).

The DNA samples (in cleavage buffer) are then mixed (0.2 μg of pSLE40 or pSLE41 and 1 μg of pSG5), heated to 70° C. and the ligase reaction conditions are set up by addition of mercaptoethanol (final concentration 10 mM) and ATP (0.1 mM). The mixture is incubated in the presence of 1 unit of T4 DNA ligase (Boehringer Mannheim) at 4° C. for 12 h. The mixture is then transformed into $E.$ $coli$ (Maniatis et al.) and, when pSLE41 is used, colonies with chloramphenicol resistance and tetracycline sensitivity are selected. pSLE40 hybdrids are tested for chloramphenicol resistance and ampicillin sensitivity. Colonies with the appropriate resistance pattern are subjected to rapid lysis to determine the plasmid sizes (T. Eckhardt, Plasmid 1 (1978) 584). DNA is isolated from cells which contain a plasmid of the required length, and restriction analysis is used to elucidate whether the expected fusion plasmids have been produced.

These plasmids are transformed into $S.$ $lividans$ TK 23 by customary processes (K. F. Chater, D. A. Hopwood, T. Kieser and C. J. Thompson: Gene Cloning in Streptomyces, Current Topics in Miroboil. and Immunol. 96, 69–95 (1982)) and selection for thiostrepton resistance is carried out. Plasmid DNA is isolated from thiostrepton-resistant *S. lividans* colonies using standard procedures (T. Kieser, Factors Affecting the Isolation of ccc DNA from *Streptomyces lividans* and *E. coli,* Plasmid 12, 19 (1984)) and its composition is checked.

All plasmids obtained from thiostrepton-resistant colonies carry the genes of the pSG5 plasmid which are necessary for replication. Thus, an appropriate "minimal replicon" can be identified from the overall results (in this case the 4.45 kb BamHI fragment), which can be further minimized by other cloning experiments and by comparative overlapping cloning.

We claim:

1. A hybrid plasmid containing an *E. coli* replicon and a Streptomycetes replicon selected from the group consisting of the replicons of the plasmids pSG2, pSG5 and pSVH1.

2. A plasmid as claimed in claim 1, in which the *E. coli* replicon is selected from the group consisting of the replicons of the plasmids pBR322, pACYC177 and pACYC184.

3. A plasmid as claimed in claim 1, which is replicated in *E. coli* and in a Streptomyces species selected from the group consisting of *S. lividans, S. geysirensis, S. ghanaensis* and *S. venezuelae.*

4. A plasmid as claimed in claim 2, which is replicated in *E. coli* and in a Streptomyces species selected from the group consisting of *S. lividans, S. geysirensis, S. ghanaensis* and *S. venezuelae.*

5. A process for preparing a hybrid plasmid as claimed in claim 1, which comprises ligating DNA containing the replicon of a plasmid selected from the group consisting of pSG2, pSVH1 and pSG5 with DNA containing an *E. coli* replicon.

6. A process as claimed in claim 5, wherein the *E. coli* replicon is selected from those of pBR322, pACYC177 and pACYC184.

* * * * *